(12) United States Patent
Styner et al.

(10) Patent No.: US 11,276,500 B2
(45) Date of Patent: Mar. 15, 2022

(54) METHODS, SYSTEMS, AND COMPUTER READABLE MEDIA FOR UTILIZING BRAIN STRUCTURAL CHARACTERISTICS FOR PREDICTING A DIAGNOSIS OF A NEUROBEHAVIORAL DISORDER

(71) Applicants: The University of North Carolina at Chapel Hill, Chapel Hill, NC (US); The Royal Institution for the Advancement of Learning/McGill University, Montreal (CA); College of Charleston, Charleston, SC (US)

(72) Inventors: Martin Andreas Styner, Chapel Hill, NC (US); Sun Hyung Kim, Durham, NC (US); Donald Louis Collins, St-Lambert (CA); Vladimir S. Fonov, Montreal (CA); Brent Carl Munsell, Mount Pleasant, SC (US); Joseph Piven, Pittsboro, NC (US); Heather Cody Hazlett, Durham, NC (US)

(73) Assignees: THE UNIVERSITY OF NORTH CAROLINA AT CHAPEL HILL, Chapel Hill, NC (US); COLLEGE OF CHARLESTON, Charleston, SC (US); THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

(21) Appl. No.: 16/235,379

(22) Filed: Dec. 28, 2018

(65) Prior Publication Data
US 2019/0148021 A1    May 16, 2019

Related U.S. Application Data

(63) Continuation of application No. PCT/US2017/040041, filed on Jun. 29, 2017.
(Continued)

(51) Int. Cl.
*G16H 50/30* (2018.01)
*G06N 3/02* (2006.01)
(Continued)

(52) U.S. Cl.
CPC ............ *G16H 50/30* (2018.01); *A61B 5/055* (2013.01); *A61B 5/4064* (2013.01);
(Continued)

(58) Field of Classification Search
None
See application file for complete search history.

(56) References Cited

U.S. PATENT DOCUMENTS 7,751,602 B2    7/2010   Collins et al.
7,899,255 B2    3/2011   Lindgren et al.
(Continued)

FOREIGN PATENT DOCUMENTS

CA    2 565 646    4/2008
CA    2 752 370    3/2013

OTHER PUBLICATIONS

Jones, Warren and Ami Klin. "Attention to eyes is present but in decline in 2-6-month-old infants later diagnosed with autism." Dec. 19, 2013; Nature; vol. 504 No. 7480, pp. 427-431. (Year: 2013).*
(Continued)

*Primary Examiner* — Rachel L. Porter
(74) *Attorney, Agent, or Firm* — Jenkins, Wilson, Taylor & Hunt, P.A.

(57) ABSTRACT

Methods, systems, and computer readable media for utilizing brain structural characteristics for predicting a diagnosis
(Continued)

of a neurobehavioral disorder are disclosed. One method for utilizing brain structural characteristics for predicting a diagnosis of a neurobehavioral disorder includes receiving brain imaging data for a human subject of at least one first age. The method also includes determining, from the brain imaging data, measurements of brain structural characteristics of the human subject and inputting the brain structural characteristics into a model that predicts, using the measurements of the brain structural characteristics, a diagnosis of a neurobehavioral disorder at a second age greater than the at least one first age.

8 Claims, 20 Drawing Sheets

Related U.S. Application Data

(60) Provisional application No. 62/356,483, filed on Jun. 29, 2016.

(51) Int. Cl.
| | | |
|---|---|---|
| A61B 5/055 | (2006.01) | |
| A61B 5/00 | (2006.01) | |
| G06N 3/08 | (2006.01) | |
| G16H 30/40 | (2018.01) | |
| G16H 50/20 | (2018.01) | |
| G06T 7/00 | (2017.01) | |
| G06N 3/04 | (2006.01) | |
| G06N 20/10 | (2019.01) | |
| G06N 7/08 | (2006.01) | |

(52) U.S. Cl.
CPC .......... *A61B 5/4076* (2013.01); *A61B 5/7267* (2013.01); *G06N 3/02* (2013.01); *G06N 3/0454* (2013.01); *G06N 3/084* (2013.01); *G06N 20/10* (2019.01); *G06T 7/0012* (2013.01); *G16H 30/40* (2018.01); *G16H 50/20* (2018.01); *A61B 2576/026* (2013.01); *G06N 7/08* (2013.01); *G06T 2207/20081* (2013.01); *G06T 2207/30016* (2013.01)

(56) References Cited

U.S. PATENT DOCUMENTS

| | | |
|---|---|---|
| 8,699,776 B2 | 4/2014 | Duschesne |
| 11,096,583 B2 | 8/2021 | Emerson et al. |
| 2011/0218253 A1 | 9/2011 | Lange et al. |
| 2013/0116540 A1 | 5/2013 | Li et al. |
| 2013/0231552 A1 | 9/2013 | Grady et al. |
| 2014/0222738 A1* | 8/2014 | Joyce .................. G06N 3/10 706/13 |
| 2014/0226882 A1 | 8/2014 | Collins et al. |
| 2015/0080703 A1* | 3/2015 | Reiman .............. A61B 5/4848 600/409 |
| 2015/0272461 A1* | 10/2015 | Morimoto ............. A61B 5/055 600/410 |
| 2015/0313913 A1 | 11/2015 | Catterall et al. |
| 2019/0133446 A1 | 5/2019 | Emerson et al. |
| 2019/0209097 A1 | 7/2019 | Martien et al. |
| 2019/0287247 A1 | 9/2019 | Duchesne et al. |

OTHER PUBLICATIONS

Hazlett HC, Poe MD, Gerig G, et al. "Early Brain Overgrowth in Autism Associated With an Increase in Cortical Surface Area Before Age 2 Years." Archives of General Psychiatry, May 2011; vol. 68(5), pp. 467-476) (Year: 2011).*

Gang Li, Jingxin Nie, Li Wang, Feng Shi, John H. Gilmore, Weili Lin, Dinggang Shen, "Measuring the dynamic longitudinal cortex development in infants by reconstruction of temporally consistent cortical surfaces," NeuroImage, vol. 90, Apr. 15, 2014, pp. 266-279 (Year: 2014).*

Non-Final Office Action for U.S. Appl. No. 16/235,402 (dated Jul. 8, 2019).

Sacrey et al., "Can Parents' Concerns Predict Autism Spectrum Disorder? A Prospective Study of High-Risk Siblings From 6 to 36 Months of Age," Journal of the American Academy of Child & Adolescent Psychiatry, vol. 54, No. 6, pp. 470-478 (Jun. 2015).

"Autism—Brain Regions and their Dysfunctions," Brain Maps, https://web.archive.org/web/20090805233139/http://www.brainmaps.com/autism.html, pp. 1-4 (Aug. 5, 2009).

Notification of Transmittal of the International Search Report and the Written Opinion of the International Searching Authority, or the Declaration for International Patent Application Serial No. PCT/US 2017/040041 (dated Jun. 29, 2017).

Lenz, "Deep learning for robotics," Cornell University, pp. 1-155 (Jan. 2016).

Retico et al., "Neuroimaging-based methods for autism identification: a possible translational application?," Functional Neurology, vol. 29, No. 4, pp. 231-239 (2014).

Jones et al., "Attention to eyes is present but in decline in 2-6 month-old infants later diagnosed with autism," Nature, vol. 504, pp. 1-28 (2013).

Kim et al., "Adaptive prior probability and spatial temporal intensity change estimation for segmentation of the one-year-old human brain," Journal of Neuroscience Methods, vol. 212, No. 1, pp. 1-27 (2013).

"DSM-5," Wikipedia, https://en.wikipedia.org/wiki/DSM-5, pp. 1-17 (Mar. 5, 2019).

"Diagnostic and Statistical Manual of Mental Disorders," Wikipedia, https://en.wikipedia.org/wiki/Diagnostic_and_Statistical_Manual_of_Mental_Disorders, pp. 1-19 (Mar. 2, 2019).

"Prevalence and Characteristics of Autism Spectrum Disorder Among Children Aged 8 Years—Autism and Developmental Disabilities Monitoring Network, 11 Sites, United States, 2012," Centers for Disease Control and Prevention, Morbidity and Mortality Weekly Report, Surveillance Summaries, vol. 65, No. 13, https://www.cdc.gov/mmwr/volumes/65/ss/pdfs/ss6513a1-H.pdf, pp. 1-28 (Nov. 16, 2018).

Abu-Akel et al., "Mind the prevalence rate: overestimating the clinical utility of psychiatric diagnostic classifiers," Psychological Medicine, vol. 48, pp. 1-3 (2018).

Notification of Transmittal of the International Search Report and the Written Opinion of the International Searching Authority, or the Declaration for International Application No. PCT/US2017/040032 (dated Sep. 7, 2017).

Greene et al., "Multivariate pattern classification of pediatric Tourette syndrome using functional connectivity MRI," Developmental Science, vol. 19, No. 4, pp. 581-598 (2016).

Rosenberg et al., "A neuromarker of sustained attention from whole-brain functional connectivity," Nat. Neurosci., vol. 19, No. 1, pp. 165-171 (Jan. 2016).

Cotney et al., "The autism-associated chromatin modifier CHD8 regulates other autism risk genes during human neurodevelopment," Nature Communications, pp. 1-11 (2015).

Estes et al., "Behavioral, cognitive, and adaptive development in infants with autism spectrum disorder in the first 2 years of life," Journal of Neurodevelopmental Disorders, vol. 7, No. 24, pp. 1-10 (2015).

Pruett et al., "Accurate age classification of 6 and 12 month-old infants based on resting-state functional connectivity magnetic resonance imaging data," Developmental Cognitive Neuroscience, vol. 12, pp. 123-133 (2015).

Finn et al., "Functional connectome fingerprinting: identifying individuals using patterns of brain connectivity," Nat. Neurosci., vol. 18, pp. 1-26 (Nov. 2015).

Li et al., "A Robust Deep Model for Improved Classification of AD/MCI Patients," IEEE J Biomed Health Inform, vol. 19, No. 5, pp. 1-19 (Sep. 2015).

(56) References Cited

OTHER PUBLICATIONS

Wolff et al., "Altered corpus callosum morphology associated with autism over the first 2 years of life," Brain, vol. 138, pp. 2046-2058 (May 3, 2015).
Gao et al., "Development of human brain cortical network architecture during infancy," Brain Struct. Funct., vol. 220, No. 2, pp. 1-25 (Mar. 2015).
Green et al., "Parent-mediated intervention versus no intervention for infants at high risk of autism: a parallel, single-blind, randomised trial," Lancet. Psyc., vol. 2, pp. 133-140 (Feb. 2015).
Gabrieli et al., "Prediction as a Humanitarian and Pragmatic Contribution from Human Cognitive Neuroscience," Neuron, vol. 85, pp. 11-26 (Jan. 7, 2015).
Li et al., "A Robust Deep Learning for Improved Classification of AD/MCI Patients," Machine Learning in Medical Imaging (MLMI) Workshop, vol. 8679, pp. 240-247 (2014).
Pucilowska et al., "The 16p11.2 Deletion Mouse Model of Autism Exhibits Altered Cortical Progenitor Proliferation and Brain Cytoarchitecture Linked to the ERK MAPK Pathway," The Journal of Neuroscience, vol. 35, No. 7, pp. 3190-3200 (Feb. 18, 2015).
Charman, "Early identification and intervention in autism spectrum disorders: Some progress but not as much as we hoped," International Journal of Speech-Language Pathology, vol. 16, No. 1, pp. 15-18 (2014).
Rogers et al., "Autism treatment in the first year of life: a pilot study of infant start, a parent-implemented intervention for symptomatic infants," J. Autism. Dev. Disord., vol. 44, No. 12, pp. 1-25, (Dec. 2014).
Bernier et al., "Disruptive CHD8 mutations define a subtype of autism early in development," Cell, vol. 158, No. 2, pp. 1-27 (Jul. 17, 2014).
Buescher et al. "Costs of Autism Spectrum Disorders in the United Kingdom and the United States," JAMA Pediatr., vol. 168, pp. 721-728 (Jun. 9, 2014).
Chawarska et al., "18-Month Predictors of Later Outcomes in Younger Siblings of Children With Autism Spectrum Disorder: A Baby Siblings Research Consortium Study," J. Am. Acad. Child Adolesc Psychiatry, vol. 53, No. 12, pp. 1-18 (Dec. 2014).
Gan et al., "Deep self-taught learning for facial beauty prediction," Neurocomputing, vol. 144, pp. 295-303 (2014).
Li et al., "Mapping Longitudinal Hemispheric Structural Asymmetries of the Human Cerebral Cortex from Birth to 2 Years of Age," Cerebral Cortex, vol. 24, pp. 1289-1300 (2013).
Mirzaa et al., "Megalencephaly and Hemimegalencephaly: Breakthroughs in Molecular Etiology," American Journal of Medical Genetics Part C (Seminars in Medical Genetics), vol. 166C, pp. 156-172 (2014).
Ozonoff et al., "The broader autism phenotype in infancy: When does it emerge?," J Am Acad Child Adolesc Psychiatry, vol. 53, No. 4, pp. 1-19 (Apr. 2014).
Qureshi et al., "Opposing Brain Differences in 16p11.2 Deletion and Duplication Carriers," The Journal of Neuroscience, vol. 34, No. 34, p. 11199-11211 (Aug. 20, 2014).
Sugathan et al., "CHD8 regulates neurodevelopmental pathways associated with autism spectrum disorder in neural progenitors," PNAS, pp. E4468-E4477 (Oct. 7, 2014).
Wang et al., "Multi-atlas segmentation of subcortical brain structures via the AutoSeg software pipeline," Frontiers in Neuroinformatics, vol. 8, No. 7, pp. 1-11 (Feb. 2014).
Webb et al., "The motivation for very early intervention for infants at high risk for autism spectrum disorders," Int. J. Speech. Lang. Pathol., vol. 16, pp. 1-11 (Feb. 2014).
Wolff et al., "Longitudinal Patterns of Repetitive Behavior in Toddlers with Autism," J Child Psychol Psychiatry, vol. 55, No. 8, pp. 1-17 (Aug. 2014).
Ciresan et al., "Mitosis Detection in Breast Cancer Histology Images with Deep Neural Networks," MICCAI, Nagoya, Japan, pp. 1-8 (2013).
Georgiades et al., "A Prospective Study of Autistic-Like Traits in Unaffected Siblings of Probands With Autism Spectrum Disorder," JAMA Psychiatry, vol. 70, No. 1, pp. 42-48 (2013).
Elison et al., "White Matter Microstructure and Atypical Visual Orienting in 7-Month-Olds at Risk for Autism," Am. J. Psychiatry, vol. 170, No. 8, pp. 1-18 (Aug. 1, 2013).
Uddin et al., "Salience Network-Based Classification and Prediction of Symptom Severity in Children with Autism," JAMA Psychiatry, vol. 70, pp. 869-879 (Jun. 2013).
Fair et al., "Distinct neural signatures detected for ADHD subtypes after controlling for micro-movements in resting state functional connectivity MRI data," Frontiers in Systems Neuroscience, vol. 6, Article 80, pp. 1-31 (Feb. 4, 2013).
Guthrie et al., "Early diagnosis of autism spectrum disorder: Stability and change in clinical diagnosis and symptom presentation," J Child Psychol Psychiatry, vol. 54, No. 5, pp. 1-18 (May 2013).
Castellanos et al., "Clinical applications of the functional connectome," Neuroimage, vol. 80, pp. 1-33 (Oct. 15, 2013).
Ecker et al., "Translational approaches to the biology of Autism: false dawn or a new era?," Molecular Psychiatry, vol. 18, pp. 435-442 (2013).
Landa et al., "Developmental Trajectories in Children With and Without Autism Spectrum Disorders: The First 3 Years," Child Dev., vol. 84, No. 2, pp. 1-21 (2013).
Messinger et al., "Beyond Autism: A Baby Siblings Research Consortium Study of High-Risk Children at Three Years of Age," J Am Child Adolesc Psychiatry, vol. 52, No. 3, pp. 1-17 (Mar. 2013).
Nonaka-Kinoshita et al., "Regulation of cerebral cortex size and folding by expansion of basal progenitors," The EMBO Journal, vol. 32, pp. 1817-1828 (2013).
Raznahan et al., "Compared to What? Early Brain Overgrowth in Autism and the Perils of Population Norms," Biol Psychiatry, vol. 74, pp. 563-575 (2013).
Shen et al., "Early brain enlargement and elevated extra-axial fluid in infants who develop autism spectrum disorder," Brain, vol. 136, pp. 2825-2835 (2013).
Suk et al., "Deep Learning-Based Feature Representation for AD/MCI Classification," Medical Image Computing and Computer Assisted Intervention (MICCAI), Lecture Notes in Computer Science, vol. 16, pp. 1-11 (2013).
Satterthwaite et al., "Heterogeneous Impact of Motion on Fundamental Patterns of Developmental Changes in Functional Connectivity During Youth," Neuroimage, vol. 83, pp. 1-27 (Dec. 2013).
Turner-Brown et al., "The First Year Inventory: A longitudinal follow-up of 12-month-olds to 3 years of age," Autism, vol. 17, No. 5, pp. 1-17 (Sep. 2013).
Vergun et al., "Characterizing functional connectivity differences in aging adults using machine learning on resting state fMRI data," Frontiers in Computational Neuroscience, vol. 7, Article 38, pp. 1 (Apr. 2013).
Fishbaugh et al., "A framework for longitudinal data analysis via shape regression," Proc SPIE, pp. 1-11 (Feb. 23, 2012).
Elsabbagh et al., "Infant Neural Sensitivity to Dynamic Eye Gaze is Associated with Later Emerging Autism," Current Biology, vol. 22, pp. 338-342 (Feb. 21, 2012).
Van Dijk et al., "The Influence of Head Motion on Intrinsic Functional Connectivity MRI," Neuroimage, vol. 59, No. 1, pp. 1-19 (Jan. 2, 2012).
Emerson et al., "Early math achievement and functional connectivity in the fronto-parietal network," Developmental Cognitive Neuroscience, vol. 2S, pp. S139-S151 (2012).
Hao et al., "Gated Boltzmann Machine in Texture Modeling," International Conference on Artificial Neural Networks and Machine Learning (ICANN), Lecture Notes in Computer Science, vol. 7553, pp. 1-8 (2012).
Hazlett et al., "Brain Volume Findings in Six Month Old Infants at High Familial Risk for Autism," Am J Psychiatry, vol. 169, No. 6, pp. 1-17 (Jun. 2012).
Huang et al., "Learning Hierarchical Representations for Face Verification with Convolutional Deep Belief Networks," IEEE Conference on Computer Vision and Pattern Recognition (CVPR), pp. 1-8 (2012).

(56) References Cited

OTHER PUBLICATIONS

Shin et al., "Stacked Autoencoders for Unsupervised Feature Learning and Multiple Organ Detection in a Pilot Study Using 4D Patient Data," IEEE Transactions on Pattern Analysis and Machine Intelligence, vol. 35, No. 8, pp. 1-14 (2012).
Shaw et al., "Development of Cortical Surface Area and Gyrification in Attention-Deficit/Hyperactivity Disorder," Biol Psychiatry, vol. 72, No. 3, pp. 191-197 (2012).
Wolff et al., "Differences in White Matter Fiber Tract Development Present From 6 to 24 Months in Infants With Autism," Am. J. Psychiatry, vol. 169, pp. 589-600 (2012).
Avants et al., "A Reproducible Evaluation of ANTs Similarity Metric Performance in Brain Image Registration," Neuroimage, vol. 54, No. 3, pp. 1-28 (Feb. 1, 2011).
Chawarska et al., "Early Generalized Overgrowth in Boys with Autism," Arch Gen Psychiatry, vol. 68, No. 10, pp. 1-23 (Oct. 2011).
Fonov et al., "Unbiased Average Age-Appropriate Atlases for Pediatric Studies," Neuroimage, vol. 54, No. 1, pp. 1-34 (Jan. 1, 2011).
Constantino, "The Quantitative Nature of Autistic Social Impairment," Pediatr Res., vol. 69, No. 5 Pt 2, pp. 1-17 (May 2011).
Hazlett et al., "Early Brain Overgrowth in Autism Associated with an Increase in Cortical Surface Area Before Age 2," Arch Gen Psychiatry, vol. 68, No. 5, pp. 1-20 (May 2011).
Constantino et al., "Infant head growth in male siblings of children with and without autism spectrum disorders," J. Neurodevelop Disord, vol. 2, pp. 39-46 (2010).
Fonov et al., "Improved Precision in the Measurement of Longitudinal Global and Regional Volumentric Changes Via a Novel MRI Gradient Distortion Characterization and Correction Technique," Computer Vision—Accv 2006, Pt 1, vol. 6326, pp. 324-333 (2010).
Karmel et al., "Early Medical and Behavioral Characteristics of NICU Infants Later Classified With ASD," Pediatrics, vol. 126, No. 3, pp. 1-21 (Sep. 2010).
Dosenbach et al., "Prediction of Individual Brain Maturity Using fMRI," Science, vol. 329, No. 5997, pp. 1-9 (Sep. 10, 2010).
Sladky et al., "Slice-timing effects and their correction in functional MRI," NeuroImage, vol. 58, pp. 588-594 (2011).
Power et al., "Methods to detect, characterize, and remove motion artifact in resting state fMRI," Neuroimage, vol. 84, pp. 1-45 (Jan. 2014).
Developmental Disabilities Monitoring Network, "Prevalence of Autism Spectrum Disorder Among Children Aged 8 Years—Autism and Developmental Disabilities Monitoring Network, 11 Sites, United States, 2010," Morbidity and Mortality Weekly Report, Surveillance Summaries, vol. 63, No. 2, pp. 1-24 (Mar. 28, 2014).
Marrus et al., "Lack of Effect of Risperidone on Core Autistic Symptoms: Data from a Longitudinal Study," Journal of Child Adolescent Psychopharmacology, vol. 24, No. 9, pp. 513-518 (2014).
Fang et al., "Overproduction of Upper-Layer Neurons in the Neocortex Leads to Autism-like Features in Mice," Cell Reports, vol. 9, pp. 1-10 (2014).
Power et al., "Spurious but systematic correlations in functional connectivity MRI networks arise from subject motion," Neuroimage, vol. 59, No. 3, pp. 1-28 (Feb. 1, 2012).
Philip et al., "A systematic review and meta-analysis of the fMRI investigation of autism spectrum disorders," Neuroscience and Biobehavioral Reviews, vol. 36, pp. 901-942 (2012).
Ozonoff et al., "Recurrence Risk for Autism Spectrum Disorders: A Baby Siblings Research Consortium Study," Pediatrics, vol. 128, No. 3, pp. e488-e495 (Sep. 2011).
Power et al., "Functional network organization of the human brain," Neuron, vol. 72, No. 4, pp. 1-25 (Nov. 17, 2011).
Kim et al., "Functions of GSK-3 signaling in development of the nervous system," Frontiers in Molecular Neuroscience, vol. 4, No. 44, pp. 1-13 (2011).
Piven, Specific Aims, NIH Research Project Grant Program Proposal, p. 1 (2011).
Hill et al., "Similar patterns of cortical expansion during human development and evolution," PNAS, vol. 107, No. 29, pp. 13135-13140 (Jul. 20, 2010).
Hinton, "A Practical Guide to Training Restricted Boltzmann Machines," UTML TR, pp. 1-21 (Aug. 2, 2010).
Dawson et al., "Randomized, Controlled Trial of an Intervention for Toddlers With Autism: The Early Start Denver Model," Pediatrics, vol. 125, pp. 1-15 (Jan. 2010).
Ozonoff et al., "A Prospective Study of the Emergence of Early Behavioral Signs of Autism," J Am Acad Child Adolesc Psychiatry, vol. 49, No. 3, pp. 1-18 (Mar. 2010).
Schumann et al., "Longitudinal MRI Study of Cortical Development through Early Childhood in Autism," J Neurosci, vol. 30, No. 12, pp. 1-24 (Mar. 24, 2010).
Tustison et al., "N4ITK: Improved N3 Bias Correction," IEEE Trans Med Imaging, vol. 29, No. 6, pp. 1-23 (Jun. 2010).
Winkler et al., "Cortical Thickness or Grey Matter Volume? The Importance of Selecting the Phenotype for Imaging Genetics Studies," Neuroimage, vol. 53, No. 3, pp. 1-28 (Nov. 15, 2010).
Mirenda et al., "Validating the Repetitive Behavior Scale-Revised in Young Children with Autism Spectrum Disorder," J. Autism Dev. Disord., vol. 40, pp. 1521-1530 (2010).
Piven, NIH Research Project Grant Program Proposal, pp. 1-19 (2010).
Piven, Response to Reviewers' Feedback, NIH Research Project Grant Program Proposal, p. 1 (2010).
Yirmiya et al., "The prodrome of autism: Early behavioral and biological signs, regression, peri- and post-natal development and genetics," Journal of Child Psychology and Psychiatry, vol. 51, pp. 1-89 (2010).
Shehzad et al., "The Resting Brain: Unconstrained yet Reliable," Cerebral Cortex, vol. 19, No. 10, pp. 2209-2229 (Oct. 2009).
Pereira et al., "Machine learning classifiers and fMRI: a tutorial overview," Neuroimage, vol. 45, pp. 1-24 (Mar. 2009).
Hastie et al., "The Elements of Statistical Learning: Data Mining, Inference and Prediction," Second Edition, Springer, pp. 1-764 (2009).
Lee et al., "Unsupervised feature learning for audio classification using convolutional deep belief networks," Advances in Neural Information Processing Systems (NIPS), pp. 1-9 (2009).
Lee et al., "Convolutional Deep Belief Networks for Scalable Unsupervised Learning of Hierarchical Representations," 26th Annual International Conference on Machine Learning (ICML), pp. 1-8 (2009).
Panizzon et al., "Distinct Genetic Influences on Cortical Surface Area and Cortical Thickness," Cerebral Cortex, vol. 19, pp. 2728-2735 (2009).
Shaw et al., "Neurodevelopmental Trajectories of the Human Cerebral Cortex," The Journal of Neuroscience, vol. 28, No. 14, pp. 3586-3594 (Apr. 2, 2008).
Im et al., "Brain Size and Cortical Structure in the Adult Human Brain," Cerebral Cortex, vol. 18, pp. 2181-2191 (Sep. 2008).
Avants et al., "Symmetric Diffeomorphic Image Registration with Cross-Correlation: Evaluating Automated Labeling of Elderly and Neurodegenerative Brain," Med Image Anal, vol. 12, No. 1, pp. 1-29 (Feb. 2008).
Knickmeyer et al., "A Structural MRI Study of Human Brain Development from Birth to 2 Years," J Neurosci, vol. 28, No. 47, pp. 1-17 (Nov. 19, 2008).
Ganz, "The Lifetime Distribution of the Incremental Societal Costs of Autism," Arch. Pediatr. Adolesc. Med., vol. 161, pp. 343-349 (Apr. 2007).
Gilmore et al., "Regional Gray Matter Growth, Sexual Dimorphism, and Cerebral Asymmetry in the Neonatal Brain," J Neurosci., vol. 27, No. 6, pp. 1-17 (Feb. 2007).
Piven, "III. Research Plan," PHS 398/2590, p. 238 (Apr. 2006).
Benjamini et al., "Adaptive Linear Step-up Procedures that control the False Discovery Rate," Biometricka, vol. 93, No. 3, pp. 1-25 (2006).
Casanova et al., "Minicolumnar abnormalities in autism," Acta Neuropathol, vol. 112, No. 3, pp. 287-303 (2006).
Hinton et al., "Reducing the Dimensionality of Data with Neural Networks," Science, vol. 313, pp. 504-507 (2006).

(56) References Cited

OTHER PUBLICATIONS

Hazlett et al., "Magnetic Resonance Imaging and Head Circumference Study of Brain Size in Autism: Birth Through Age 2 Years," Arch Gen Psychiatry, vol. 62, pp. 1366-1376 (2005).
Zou et al., "Regularization and variable selection via the elastic net," J of the Royal Statistical Society, Series B, Statistical Methodology, vol. 67, No. 2, pp. 301-320 (2005).
Zwaigenbaum et al., "Behavioral manifestations of autism in the first year of life," Int. J. Devl Neuroscience, vol. 23, pp. 143-152 (2005).
Mathias et al., "Algorithms for Spectral Analysis of Irregularly Sampled Time Series," Journal of Statistical Software, vol. 11, Issue 2, pp. 1-27 (May 2004).
Wetherby et al. "Early Indicators of Autism Spectrum Disorders in the Second Year of Life," Journal of Autism and Developmental Disorders, vol. 34, No. 5, pp. 473-493 (Oct. 2004).
Wetherby et al., "Validity and Reliability of the Communication and Symbolic Behavior Scales Developmental Profile With Very Young Children," Journal of Speech, Language, and Hearing Research, vol. 45, pp. 1202-1218 (Dec. 2002).
Chenn et al., "Regulation of Cerebral Cortical Size by Control of Cell Cycle Exit in Neural Precursors," Science, vol. 297, pp. 1-6 (2002).
Sparks et al., "Brain structural abnormalities in young children with autism spectrum disorder," Neurology, vol. 59, pp. 1-11 (2002).
Tzourio-Mazoyer et al., "Automated Anatomical Labeling of Activations in SPM Using a Macroscopic Anatomical Parcellation of the MNI MRI Single-Subject Brain," NeuroImage, vol. 15, pp. 273-289 (2002).
Courchesne et al., "Unusual brain growth patterns in early life in patients with autistic disorder: An MRI study," Neurology, vol. 57, pp. 245-254 (2001).
Wetherby et al., "Communication and Symbolic Behavior Scales Developmental Profile," Baltimore, MD: Paul H. Brookes, pp. 1-8 (2001).
Lord et al., "The Autism Diagnostic Observation Schedule—Generic: A Standard Measure of Social and Communication Deficits Associated with the Spectrum of Autism," Journal of Autism and Developmental Disorders, vol. 30, No. 3, pp. 205-223 (Jun. 2000).
Bodfish et al., "Varieties of Repetitive Behavior in Autism: Comparisons to Mental Retardation," Journal of Autism and Developmental Disorders, vol. 30, No. 3, pp. 237-243 (2000).
Giedd et al., "Brain development during childhood and adolescence: a longitudinal MRI study," Nature Neuroscience, vol. 2, pp. 1-3 (1999).
Friston et al., "Movement-related effects in fMRI time-series," Magn. Reson. Med., vol. 35, No. 3, pp. 1-28 (1996).
Cortes et al., "Support-Vector Networks," Machine Learning, vol. 20, No. 3, pp. 273-297 (1995).
Mullen, "Mullen Scales of Early Learning: AGS Edition," Circle Pines, MN: American Guidance Service, Inc., pp. 1-6 (Aug. 2015).
Piven et al., "An MRI Study of Brain Size in Autism," Am J Pyschiatry, vol. 152, pp. 1145-1149 (1995).
Rakic, "A small step for the cell, a giant leap for mankind: a hypothesis of neocortical expansion during evolution," Trends Neurosci, vol. 18, pp. 383-388 (1995).
Lord et al., "Autism Diagnostic Interview—Revised: A Revised Version of a Diagnostic Interview for Caregivers of Individuals with Possible Pervasive Developmental Disorders," Journal of Autism and Developmental Disorders, vol. 24, No. 5, pp. 659-685 (1994).
Piven et al., "Magnetic Resonance Imaging in Autism: Measurement of the Cerebellum, Pons, and Fourth Ventricle," Biol Psychiatry, vol. 31, pp. 491-504 (1992).
Fearnley et al., "Ageing and Parkinson's Disease: Substantia Nigra Regional Selectivity," Brain, vol. 114, pp. 2283-2301 (1991).
Autism Diagnostic Technology, "Transforming the Diagnosis of Autism," Wayback Machine, https://web.archive.org/web/20180804180716/http://autismdiagnostictechnology.com/, pp. 1-2 (Accessed Aug. 4, 2018).
Final Office Action for U.S. Appl. No. 16/235,402 (dated Dec. 26, 2019).
Applicant-Initiated Interview Summary for U.S. Appl. No. 16/235,402 (dated Sep. 11, 2019).
Advisory Action for U.S. Appl. No. 16/235,402 (dated Apr. 10, 2020).
Applicant-Initiated Interview Summary for U.S. Appl. No. 16/235,402 (dated Mar. 25, 2020).
Non-Final Office Action for U.S. Appl. No. 16/235,402 (dated Jul. 22, 2020).
Final Office Action for U.S. Appl. No. 16/235,402 (dated Nov. 13, 2020).
Applicant-Initiated Interview Summary for U.S. Appl. No. 16/235,402 (dated Oct. 27, 2020).
Jin et al., "Identification of Infants at High-Risk for Autism Spectrum Disorder Usiing Multiparameter Multiscale White Matter Connectivity Networks," Human Brain Mapping, vol. 36, pp. 4880-4896 (2015).
Kuhn et al., "Chapter 19: An Introduction to Feature Selection," Applied Predictive Modeling, pp. 487-519 (2013).
Nielsen et al., "Multisite functional connectivity MRI classification of autism: ABIDE results," Frontiers in Human Neuroscience, pp. 1-12 (2013).
Notice of Allowance for Final Office Action for U.S. Appl. No. 16/235,402 (dated Apr. 14, 2021).
Advisory Action for U.S. Appl. No. 16/235,402 (dated Feb. 26, 2021).
Applicant-Initiated Interview Summary for U.S. Appl. No. 16/235,402 (dated Feb. 10, 2021).

* cited by examiner

| | LR (N=117) | | HR-neg (N=248) | | HR-ASD (N=70) | | P |
|---|---|---|---|---|---|---|---|
| | N | (%) | N | (%) | N | (%) | |
| Sex | | | | | | | <0.01 |
| Female | 48 | (41) | 106 | (43) | 12 | (17) | |
| Male | 69 | (59) | 142 | (57) | 58 | (83) | |
| Race | | | | | | | 0.14 |
| Non-white | 15 | (13) | 29 | (12) | 9 | (13) | |
| White | 102 | (87) | 213 | (86) | 61 | (87) | |
| Not reported | 0 | (0) | 6 | (2) | 0 | (0) | |
| Family Income | | | | | | | 0.13 |
| Not Answered | 5 | (4) | 20 | (8) | 1 | (2) | |
| <50K | 17 | (15) | 52 | (21) | 19 | (27) | |
| 50-75K | 27 | (23) | 42 | (17) | 17 | (24) | |
| 75-100K | 20 | (17) | 40 | (16) | 12 | (17) | |
| 100-150K | 29 | (25) | 50 | (20) | 12 | (17) | |
| >150K | 19 | (16) | 44 | (18) | 9 | (13) | |
| Mother's Highest Education | | | | | | | <0.01 |
| Not Answered | 0 | (0) | 8 | (3) | 0 | (0) | |
| No College | 16 | (14) | 75 | (30) | 29 | (41) | |
| College Degree | 47 | (40) | 108 | (44) | 25 | (36) | |
| Graduate Degree | 54 | (46) | 57 | (23) | 16 | (23) | |
| | Mean | (SD) | Mean | (SD) | Mean | (SD) | |
| Mother's Age at Child Birth | | | | | | | 0.99 |
| Years | 33.2 | (4.2) | 33.2 | (4.7) | 33.3 | (4.1) | |
| Birth Weight | | | | | | | 0.52 |
| Pounds (LB) | 8.0 | (1.0) | 7.9 | (1.0) | 7.9 | (1.3) | |
| Gestational Age at Birth | | | | | | | 0.30 |
| Weeks | 39.3 | (1.3) | 39.1 | (1.2) | 38.9 | (1.1) | |
| Age at Study Visit | | | | | | | |
| 6 month visit | 6.7 | (0.7) | 6.6 | (0.7) | 6.6 | (0.7) | 0.54 |
| 12 month visit | 12.7 | (0.7) | 12.7 | (0.6) | 12.7 | (0.7) | 0.48 |
| 24 month visit | 24.6 | (0.8) | 24.7 | (0.9) | 24.6 | (0.6) | 0.59 |
| 24 month Behavioral Scores | | | | | | | |
| Mullen ELC | 109.7 | (13.8) | 101.8 | (15.9) | 79.3 | (17.6) | 0.01 |
| Vineland ABC | 105.0 | (7.4) | 101.0 | (9.0) | 88.1 | (10.0) | <0.01 |

FIG. 1

| Measure | Trajectory | LR[a] (N=42) | | | HR-neg[b] (N=91) | | | HR-ASD[c] (N=15) | | | Overall Group Comparison | | | Pairwise Group Comparison |
|---|---|---|---|---|---|---|---|---|---|---|---|---|---|---|
| | | Slope | SE | | Slope | SE | | Slope | SE | | df1,df2 | F | p | |
| Total brain volume | 1st Year | 24046 | 1416 | | 25329 | 980 | | 27298 | 2399 | | 2,289 | 0.72 | 0.49 | |
| | 2nd Year | 10928 | 523 | | 10277 | 360 | | 13318 | 1060 | | 2,289 | 3.83 | 0.02 | c>(a, b) |
| Surface Area | 1st Year | 972 | 71 | | 1061 | 49 | | 1331 | 125 | | 2,289 | 3.13 | 0.04 | c>(a, b) |
| | 2nd Year | 864 | 38 | | 814 | 26 | | 960 | 75 | | 2,289 | 1.93 | 0.15 | |
| Cortical Thickness | 1st Year | -0.024 | 0.003 | | -0.024 | 0.002 | | -0.024 | 0.006 | | 2,289 | 0.00 | 0.99 | |
| | 2nd Year | -0.025 | 0.002 | | -0.021 | 0.001 | | -0.025 | 0.004 | | 2,289 | 1.44 | 0.24 | |
| Cross-sectional | Visit age | LSM | SE | | LSM | SE | | LSM | SE | | df1,df2 | F | p | |
| Total brain volume | 6 months | 748890 | 9269 | | 762420 | 6297 | | 771403 | 15604 | | 2,289 | 1.08 | 0.34 | |
| | 12 months | 893167 | 11550 | | 914391 | 7843 | | 935189 | 19590 | | 2,289 | 2.10 | 0.12 | |
| | 24 months | 1024297 | 12475 | | 1037714 | 8444 | | 1095002 | 21563 | | 2,289 | 4.34 | 0.02 | c>(a, b) |
| Surface area | 6 months | 51736 | 541 | | 52611 | 367 | | 52779 | 914 | | 2,289 | 1.03 | 0.36 | |
| | 12 months | 57570 | 671 | | 58979 | 455 | | 60764 | 1144 | | 2,289 | 3.32 | 0.04 | c>a |
| | 24 months | 67933 | 765 | | 68746 | 518 | | 72281 | 1323 | | 2,289 | 4.16 | 0.02 | c>(a, b) |
| Cortical thickness | 6 months | 5.98 | 0.040 | | 5.96 | 0.027 | | 6.05 | 0.067 | | 2,289 | 0.69 | 0.50 | |
| | 12 months | 5.84 | 0.037 | | 5.82 | 0.025 | | 5.91 | 0.054 | | 2,289 | 0.82 | 0.44 | |
| | 24 months | 5.54 | 0.029 | | 5.56 | 0.020 | | 5.59 | 0.051 | | 2,289 | 0.48 | 0.62 | |

FIG. 2

|  | HR+<br>N=34 | HR-<br>N=145 |  |
|---|---|---|---|
| HR+ | 30 | 7 | 81% |
| HR- | 4 | 138 | 97% |
|  | 88% | 95% |  |
|  | 34 | 145 | 179 |
|  | A known | B known |  |

|  |  |  |  |
|---|---|---|---|
| A test | TP | FP | PPV |
| B test | FN | TN | NPV |
|  | Sensitivity | Specificity |  |
|  | TP+FN | FP+TN | FN+TN |
|  |  |  | TP+FP |
|  |  |  | (TP+FP+FN+TN) |

KEY: TP = true positive, FP = false positive, PPV = positive predictive value, NPV = negative predictive value

| Prediction Model | PPV | | NPV | | SENS | | SPEC | | ACC | |
|---|---|---|---|---|---|---|---|---|---|---|
| | AVE | STD ERR | AVE | STD ERR | AVE | STD ERR | AVE | STD ERR | AVE | STD ERR |
| DL-SVM | 82% | 3.22% | 95% | 0.93% | 78% | 3.97% | 94% | 0.97% | 91% | 0.92% |
| SL-SVM | 48% | 4.21% | 92% | 1.42% | 77% | 4.22% | 75% | 3.29% | 75% | 3.16% |
| DNC | 62% | 4.46% | 90% | 0.16% | 62% | 1.61% | 89% | 1.47% | 83% | 1.17% |
| PLA-SvM (Approach 1) | 22% | 3.75% | 81% | 1.20% | 30% | 4.55% | 74% | 1.84% | 65% | 1.87% |
| PLA-SvM (Approach 2) | 19% | 3.91% | 80% | 1.41% | 27% | 5.02% | 72% | 1.83% | 63% | 2.14% |

| | Measure | Month | Region | Description |
|---|---|---|---|---|
| 1 | CSA | 6 | 24 | Right Superior frontal gyrus, medial |
| 2 | CSA | 6 | 58 | Right Postcentral gyrus |
| 3 | CSA | 6 | 23 | Left Superior frontal gyrus: medial |
| 4 | CSA | 6 | 57 | Left Postcentral gyrus |
| 5 | ICV | 6 | N/A | N/A |
| 6 | CSA | 6 | 61 | Left Inferior parietal, but supramarginal and angular gyri |
| 7 | CSA | 12 | 26 | Right Superior frontal gyrus: medial orbital |
| 8 | CSA | 12 | 55 | Left Fusiform gyrus |
| 9 | CSA | 12 | 10 | Right Middle frontal gyrus orbital part |
| 10 | CSA | 6 | 62 | Right Inferior parietal, but supramarginal and angular gyri |
| 11 | CSA | 12 | 47 | Left Lingual gyrus |
| 12 | CSA | 12 | 21 | Left Olfactory Cortex |
| 13 | CTH | 12 | 67 | Left Precuneus |
| 14 | CSA | 12 | 89 | Left Inferior temporal gyrus |
| 15 | ICV | 12 | N/A | N/A |
| 16 | CTH | 6 | 36 | Right Posterior cingulate gyrus |
| 17 | CSA | 12 | 14 | Right Inferior frontal gyrus: triangular part |
| 18 | CTH | 6 | 23 | Left Superior frontal gyrus: medial |
| 19 | CTH | 12 | 90 | Right Inferior temporal gyrus |
| 20 | CSA | 12 | 33 | Left Median cingulate and paracingulate gyri |
| 21 | CSA | 12 | 61 | Left Inferior parietal, but supramarginal and angular gyri |
| 22 | CSA | 12 | 6 | Right Superior frontal gyrus: orbital part |
| 23 | CSA | 12 | 18 | Right Rolandic operculum |
| 24 | CSA | 12 | 22 | Right Olfactory Cortex |
| 25 | CSA | 12 | 68 | Right Precuneus |
| 26 | CTH | 6 | 11 | Left Inferior frontal gyrus: opercular part |
| 27 | CSA | 12 | 84 | Right Temporal pole: superior temporal gyrus |
| 28 | CSA | 12 | 90 | Right Inferior temporal gyrus |
| 29 | CTH | 6 | 79 | Left Heschl gyrus |
| 30 | CSA | 12 | 27 | Left Gyrus Rectus |
| 31 | CTH | 6 | 80 | Right Heschl gyrus |
| 32 | CSA | 6 | 47 | Left Lingual gyrus |
| 33 | CSA | 6 | 34 | Right Median cingulate and paracingulate gyri |
| 34 | CSA | 12 | 25 | Left Superior frontal gyrus: medial orbital |
| 35 | CSA | 6 | 55 | Left Fusiform gyrus |
| 36 | CTH | 12 | 39 | Left Parahippocampal gyrus |
| 37 | CTH | 12 | 65 | Left Angular gyrus |
| 38 | CTH | 6 | 35 | Left Posterior cingulate gyrus |
| 39 | CSA | 12 | 34 | Right Median cingulate and paracingulate gyri |
| 40 | CTH | 12 | 81 | Left Superior temporal gyrus |

| | Measure | Month | Region | Description |
|---|---|---|---|---|
| 1 | CSA | 6 | 24 | Right Superior frontal gyrus: medial |
| 2 | CSA | 6 | 23 | Left Superior frontal gyrus: medial |
| 3 | CSA | 6 | 58 | Right Postcentral gyrus |
| 4 | CSA | 6 | 57 | Left Postcentral gyrus |
| 5 | CSA | 6 | 61 | Left Inferior parietal, but supramarginal and angular gyri |
| 6 | CSA | 6 | 62 | Right Inferior parietal, but supramarginal and angular gyri |
| 7 | CTH | 6 | 27 | Left Gyrus Rectus |
| 8 | CSA | 6 | 34 | Right Median cingulate and paracingulate gyri |
| 9 | ICV | 6 | N/A | N/A |
| 10 | CSA | 6 | 55 | Left Fusiform gyrus |
| 11 | CSA | 6 | 59 | Left Superior parietal gyrus |
| 12 | CSA | 6 | 47 | Left Lingual gyrus |
| 13 | CTH | 6 | 83 | Left Temporal pole: superior temporal gyrus |
| 14 | CSA | 6 | 40 | Right Parahippocampal gyrus |
| 15 | CSA | 12 | 56 | Right Fusiform gyrus |
| 16 | CTH | 6 | 43 | Left Calcarine fissure and surrounding cortex |
| 17 | CTH | 6 | 34 | Right Median cingulate and paracingulate gyri |
| 18 | CSA | 12 | 34 | Right Median cingulate and paracingulate gyri |
| 19 | CSA | 6 | 49 | Left Superior occipital gyrus |
| 20 | CTH | 6 | 82 | Right Superior temporal gyrus |
| 21 | CSA | 6 | 4 | Right Superior frontal gyrus: dorsolateral |
| 22 | CTH | 6 | 51 | Left Middle occipital gyrus |
| 23 | CTH | 6 | 84 | Right Temporal pole: superior temporal gyrus |
| 24 | CSA | 6 | 89 | Left Inferior temporal gyrus |
| 25 | CSA | 6 | 48 | Right Lingual gyrus |
| 26 | ICV | 12 | N/A | N/A |
| 27 | CSA | 6 | 68 | Right Precuneus |
| 28 | CSA | 12 | 68 | Right Precuneus |
| 29 | CSA | 6 | 28 | Right Gyrus Rectus |
| 30 | CSA | 6 | 39 | Left Parahippocampal gyrus |
| 31 | CTH | 6 | 56 | Right Fusiform gyrus |
| 32 | CTH | 6 | 86 | Right Middle temporal gyrus |
| 33 | CTH | 6 | 39 | Left Parahippocampal gyrus |
| 34 | CTH | 6 | 90 | Right Inferior temporal gyrus |
| 35 | CSA | 6 | 6 | Right Superior frontal gyrus: orbital part |
| 36 | CSA | 6 | 1 | Left Precentral gyrus |
| 37 | CTH | 6 | 80 | Right Heschl gyrus |
| 38 | CTH | 6 | 22 | Right Olfactory Cortex |
| 39 | CSA | 12 | 18 | Right Rolandic operculum |
| 40 | CSA | 6 | 83 | Left Temporal pole: superior temporal gyrus |

METHODS, SYSTEMS, AND COMPUTER READABLE MEDIA FOR UTILIZING BRAIN STRUCTURAL CHARACTERISTICS FOR PREDICTING A DIAGNOSIS OF A NEUROBEHAVIORAL DISORDER

PRIORITY CLAIM

This application is a continuation of International Application No. PCT/US17/40041, which claims the priority benefit of U.S. Provisional Patent Application Ser. No. 62/356,483, filed Jun. 29, 2016, the disclosures of which are incorporated by reference herein in their entireties.

GOVERNMENT INTEREST

This invention was made with government support under Grant Nos. HD055741 and HD079124 awarded by the National Institutes of Health. The government has certain rights in the invention.

TECHNICAL FIELD

The subject matter described herein relates to medical imaging analysis. More specifically, the subject matter relates to methods, systems, and computer readable media for utilizing brain structural characteristics for predicting a diagnosis of a neurobehavioral disorder.

BACKGROUND

Despite tremendous research efforts, autism still confers substantial burden to affected individuals, their families, and the community. Early intervention is critical, but the earliest we can currently diagnose autism via observational/behavioral criteria is 24 month or later. Further, such diagnosis depends on a subjective clinical evaluation of behaviors that begin to emerge around this time.

SUMMARY

Methods, systems, and computer readable media for utilizing brain structural characteristics for predicting a diagnosis of a neurobehavioral disorder are disclosed. One method for utilizing brain structural characteristics for predicting a diagnosis of a neurobehavioral disorder includes receiving brain imaging data for a human subject of at least one first age. The method also includes determining, from the brain imaging data, measurements of brain structural characteristics of the human subject and inputting the brain structural characteristics into a model that predicts, using the measurements of the brain structural characteristics, a diagnosis of a neurobehavioral disorder at a second age greater than the at least one first age.

A system for utilizing brain structural characteristics for predicting a diagnosis of a neurobehavioral disorder is also disclosed. The system comprises at least one processor and a neurobehavioral disorder diagnosis module (ADM) implemented using the at least one processor. The ADM is configured for receiving brain imaging data for a human subject of at least one first age, for determining, from the brain imaging data, measurements of brain structural characteristics of the human subject, and for inputting the brain structural characteristics into a model that predicts, using the measurements of the brain structural characteristics, a diagnosis of a neurobehavioral disorder at a second age greater than the at least one first age.

The subject matter described herein can be implemented in software in combination with hardware and/or firmware. For example, the subject matter described herein can be implemented in software executed by at least one processor. In one example implementation, the subject matter described herein may be implemented using at least one computer readable medium having stored thereon computer executable instructions that when executed by at least one processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the terms "node" and "host" refer to a physical computing platform or device including one or more processors and memory.

As used herein, the terms "function" and "module" refer to software in combination with hardware and/or firmware for implementing features described herein.

BRIEF DESCRIPTION OF THE DRAWINGS

Some embodiments of the subject matter described herein will now be explained with reference to the accompanying drawings, wherein like reference numerals represent like parts, of which:

FIG. 1 depicts a table containing various demographic data about subjects;

FIG. 2 depicts a table containing data related to the trajectory of cortical growth using surface area (SA) and cortical thickness (CT) measurements;

FIG. 3 depicts a table containing information about a prediction model using cortical data to classify groups at 24 months;

FIG. 16 depicts a table containing mean and standard error results of 10-fold cross validation procedure for various prediction models;

FIG. 17 depicts a table containing the top 40 features contributing to the deep learning dimensionality reduction approach;

FIG. 18 depicts a table containing the top 40 features contributing to the linear sparse learning classification;

DETAILED DESCRIPTION

Figure 4:
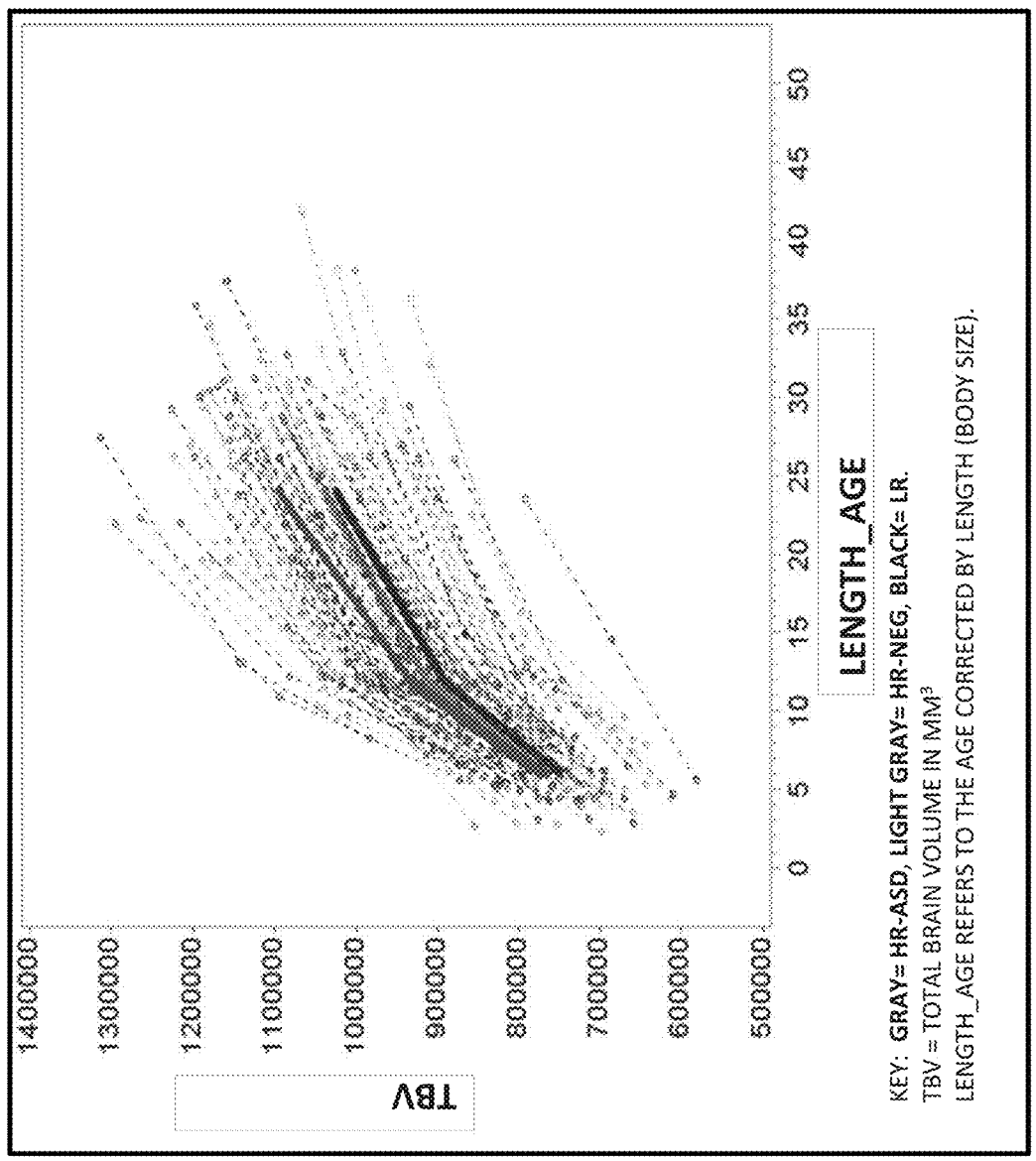
FIG. 4 depicts a graph indicating total brain volume growth for various subjects.

The subject matter described herein involves methods, systems, and computer readable media for utilizing brain structural characteristics for predicting a diagnosis of a neurobehavioral disorder. Reference will now be made in detail to various embodiments of the subject matter described herein, examples of which are illustrated in the accompanying drawings. Wherever possible, the same reference numbers will be used throughout the drawings to refer to the same or like parts.

Autism spectrum disorder (ASD) affects approximately one in 68 children [1] and is often a significant lifelong burden for affected individuals and their families. Reports of brain overgrowth in ASD have appeared in the literature over the last two decades. We first reported increased brain volume in adolescents and adults with ASD over twenty years ago [2], replicating this finding several years later [3]. Subsequent reports suggested that brain overgrowth in ASD may be most apparent in early childhood [4-8]. More recently, a small study of infants at risk for ASD found enlarged brain volume present at 12 and 24 months in ten infants later diagnosed with autism at 24 months of age [9]. Although one of the most consistently replicated brain findings in ASD, the onset, course and nature of brain overgrowth remains poorly characterized and understood.

High familial risk infant studies have provided an important paradigm for studying the early development of autism. These studies, largely focused on examining behavioral trajectories, have found that characteristic social deficits in ASD emerge during the latter part of the first and early in the second year of life [10, 11]. Retrospective head circumference and longitudinal brain volume studies of 2 to 4 year olds have provided indirect evidence that increased brain volume may emerge during this same period [5,12], with brain volume correlated with cortical surface area (SA) but not cortical thickness (CT) [6]. These observations suggest that prospective brain imaging studies of infants at high familial risk for ASD might identify early post-natal changes in brain volume occurring before the emergence of an ASD diagnosis, suggesting new insights into brain mechanisms and potential biomarkers for use in early, prodromal detection.

In the study associated with the present specification, 318 infants at high familial risk for ASD (HR), including 70 who met clinical best-estimate criteria for ASD (HR-ASD) and 248 who did not meet criteria for ASD (HR-negative or HR-neg) at 24 months of age; and 117 infants at low familial risk (LR) for ASD, who also did not meet criteria for ASD at 24 months were examined (see Methods and Supplementary Information regarding exclusionary criteria for LR). Infants were evaluated at 6, 12 and 24 months with detailed behavioral assessments and high-resolution brain magnetic resonance imaging (MRI), to prospectively investigate brain and behavioral trajectories during infancy. Details on the diagnostic criteria and image processing procedures are provided in the Methods and in Supplementary Information. Based on our prior MRI and head circumference studies we hypothesized that brain overgrowth in ASD begins before 24 months of age and that overgrowth is associated with hyper-expansion of cortical surface area. Given the correspondence between the estimated timing of brain overgrowth from our previous findings, and emerging reports about the onset of autistic behaviors from prospective high risk infant sibling studies, we further hypothesized that these early brain changes are linked to the emergence of the defining behaviors of ASD. Finally, we sought to examine whether differences in the development of brain characteristics might suggest early biomarkers (i.e., occurring prior to the onset of the defining behaviors of ASD) for the detection of later emerging ASD.

Developmental Trajectories of Brain Volume and Cortical Surface Characteristics

FIG. 1 shows various demographic data about subjects. No significant group differences (between HR-ASD, HR-neg and LR) were observed in race/ethnicity, family income, maternal age at birth, infant birth weight, gestational age at birth, or age at visit. As expected based on the well-known disproportionately higher rates of ASD in males, the HR-ASD group contained significantly more males than the LR group ($\chi$ [2](2)=15.7, p<0.01). We also observed that the LR group had higher maternal education compared to the other two groups ($\chi$ [2](2)=36.4, p<0.01). Group scores on the Mullen Scales of Infant Development [13] (Mullen) and Vineland Adaptive Behavior Scales [14] (Vineland) appear in table 100 of FIG. 1. The HR-ASD group had significantly lower Mullen and Vineland scores at 24 months than the other two groups.

Primary analyses examined group differences in trajectories of brain growth. FIG. 2 shows group differences in developmental trajectories and cross-sectional volumes by age. FIG. 4 shows the longitudinal trajectories of total brain volume (TBV) from 6 to 24 months for the three groups examined. The HR-ASD group looks similar to the HR-neg and LR groups at 6 months, but increased growth over time resulting significantly enlarged TBV compared to both HR-neg and LR groups by 24 months. The LR group trajectory, shown in black, is partially obscured by the HR-neg line, shown in light gray.

Total brain volume (or TBV) growth, was observed to show no group differences in the first year of life (6-12 months). However, the brain HR-ASD group showed significantly faster rates of TBV growth in the second year compared to LR and HR-neg groups (see FIG. 2 and FIG. 4). Pairwise comparisons at 24 months showed medium to large effect sizes for HR-ASD vs LR (Cohen's d=0.88) and HR-ASD vs HR-neg (Cohen's d=0.70).

Figure 5:
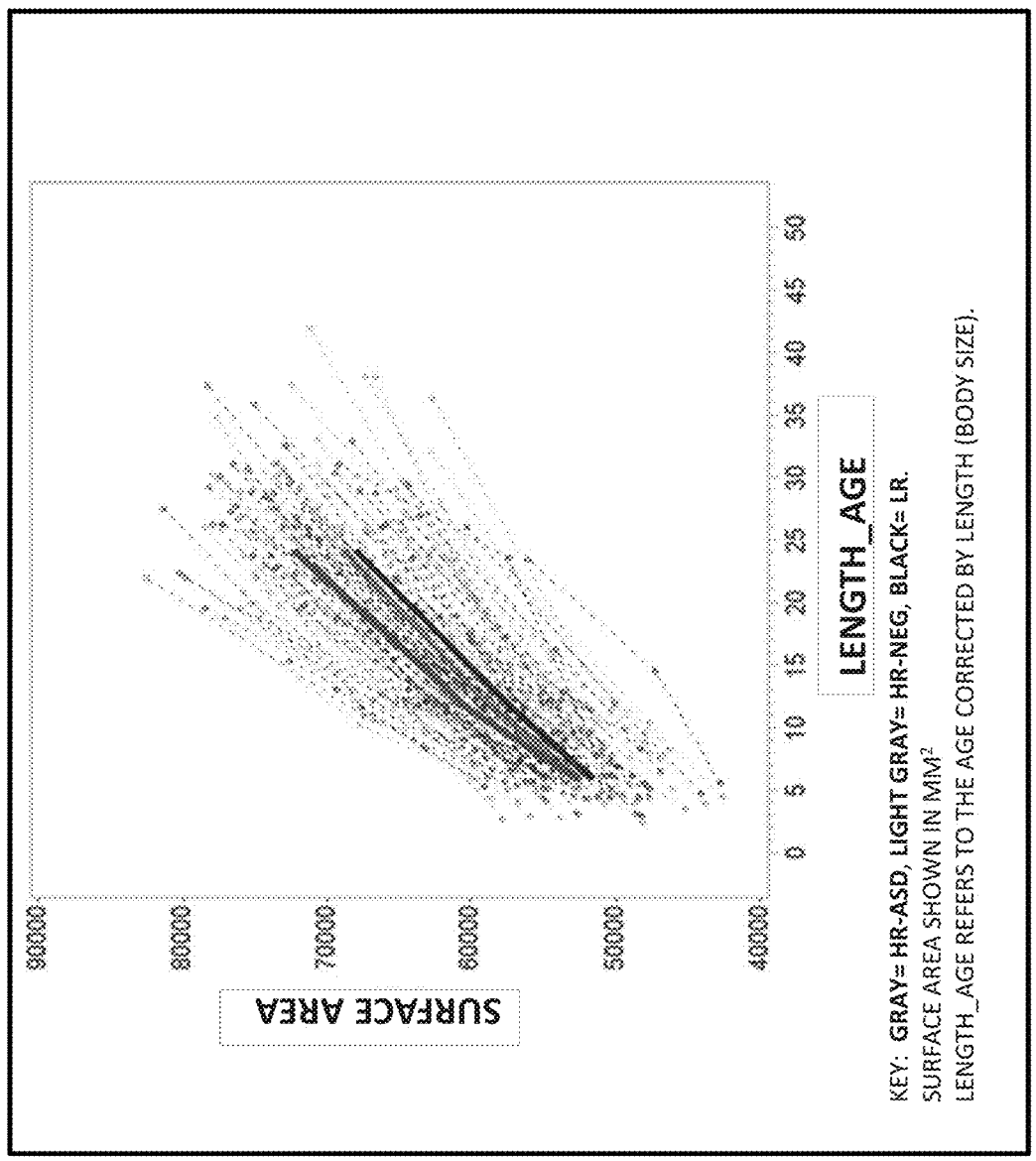
FIG. 5 depicts a graph indicating brain surface area growth for various subjects.

Groups were also compared on the trajectory of cortical growth using surface area (SA) and cortical thickness (CT) measurements. FIG. 5 shows the longitudinal trajectories of surface area from 6 to 24 months for the three groups examined. For surface area (SA), the three groups look similar at 6 months, but by 12 months the HR-ASD demonstrates a significantly steeper slope in SA between 6 and 12 months, resulting in significantly increased SA by 24 months compared to both HR-neg and LR groups.

Figure 6:
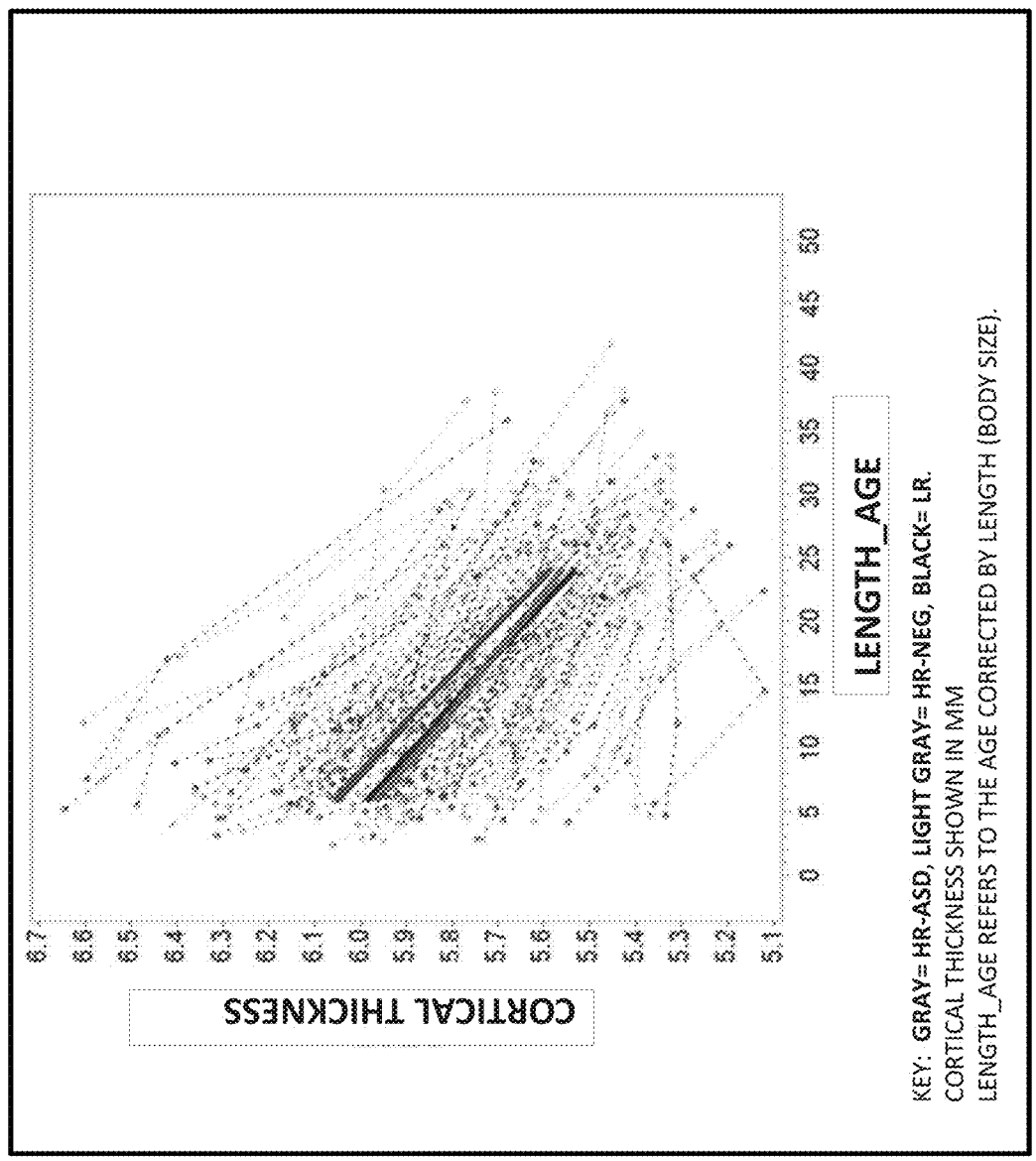
FIG. 6 depicts a graph indicating cortical thickness growth for various subjects.

We observed that the HR-ASD group showed a significant faster increase in SA in the first year of life (6-12 m) when compared to the HR-neg (t (289)=2.01, p=0.04) and LR groups (t(289)=2.50, p=0.01), but there were no significant group differences in growth rates in the second year (see FIG. 2 and FIGS. 5 and 6). Pairwise comparisons in SA at 12 months showed medium effect sizes for HR-ASD vs LR (Cohen's d=0.74) and HR-ASD vs HR-neg (Cohen's d=0.41), becoming more robust by 24 months with HR-ASD vs LR (Cohen's d=0.88) and HR-ASD vs HR-neg (Cohen's d=0.70).

FIG. 6 shows the longitudinal trajectories of cortical thickness from 6 to 24 months for the three groups examined. There are no significant group differences in trajectories for cortical thickness (CT), with all groups showing a pattern of decreasing CT over time. No group differences were observed in trajectory of CT growth in either the first (F (2,289)=0.00; p=0.99) or second years (F (2,289)=1.44; p=0.24).

To examine the regional distribution of increased SA change rate from 6-12 months of age in the HR-ASD group, exploratory analyses were conducted with a 78 region of interest surface map [19], using an adaptive Hochberg method of q<0.05 [20].

Figure 7:
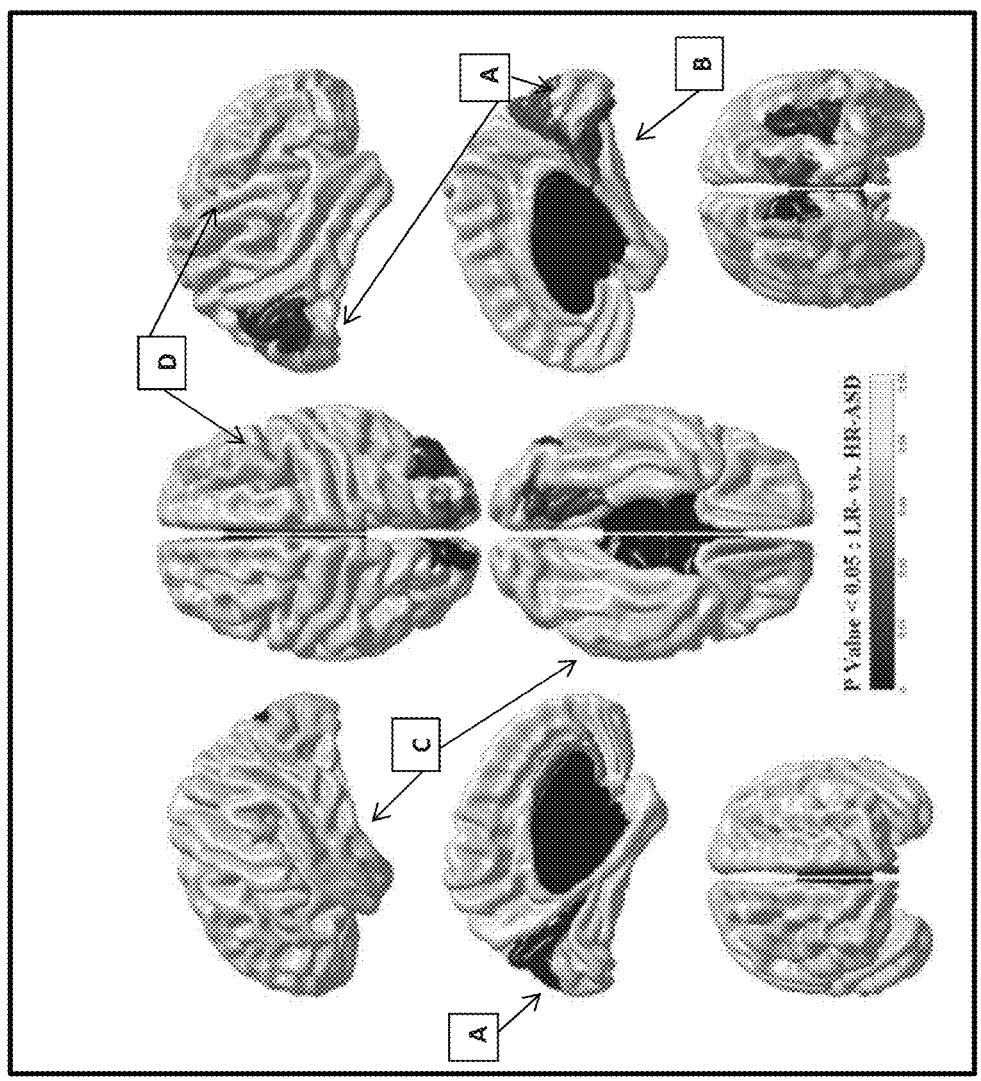
FIG. 7 shows cortical regions exhibiting significant expansion in surface area from 6-12 months.

FIG. 7 shows cortical regions exhibiting significant expansion in surface area from 6-12 months in HR-ASD. In FIG. 7, the darkened areas show the group effect for the HR-ASD versus LR subjects. The HR-ASD group had significant expansion in cortical surface area in regions that include left/right cuneus (A) and right lingual gyrus (B), and to a lesser extent the left inferior temporal gyrus (A), and middle frontal gyrus (C) as compared to the LR group.

Behavioral Correlates of Brain Overgrowth

To gain insight into the pathophysiological processes underlying the emergence of autistic behavior, we explored whether rate of volume overgrowth was linked to autism symptom severity. Pearson correlations between TBV and behavioral measures (E.G., Autism Diagnostic Observation Schedule (ADOS) and Communication and Symbolic Behavior Scales (CSBS) scores) were run adjusting for multiple comparisons.

The relationship between autistic behavior (ADOS severity score) at 24 months was examined in relationship to TBV change rate from 6-12 and 12-24 months in the HR group. No significant correlation was observed between 24 month ADOS severity and 6-12 month TBV change rate (r=0.14; p=0.06); whereas a significant correlation was noted between 24 month ADOS severity and 12-24 month TBV change rate (r=0.16; p=0.03). Subsequent analyses to examine the components of overall autism severity revealed a significant correlation between 12-24 month TBV change rate and 24 month ADOS social affect score (r=0.17, p=0.01), but not ADOS restricted/repetitive behavior score (r=0.07; p=0.31).

We further examined the relationship between TBV change rate and 24 month social behavior with an independent measure of social behavior, the Communication and Symbolic Behavior Scales [21] (CSBS). Consistent with the findings from the above ADOS analysis, the lower CSBS social composite score was significantly correlated with a more rapid TBV change rate from 12-24 months (r=0.18, p=0.03) in HR subjects, but no significant correlations were observed between CSBS scores at 24 months and TBV change rate from 6-12 months in either the CSBS total score (r=0.08, p=0.32) or CSBS social composite score (r=0.11, p=0.17).

As opposed to the ADOS, which was first administered at 24 months (the ADOS was used primarily as a tool for diagnosing ASD), measurements of social behavior were available from the CSBS at both 12 and 24 months. Consistent with a previous report of increasing/unfolding social deficits in ASD from 12-24 months of age [10], we sought to examine change in social behavior during the second year, concurrent with our observation of changes in brain volume during that same period in the HR-ASD group. We observed a significant group (HR-ASD vs. HR-neg)×time (12-24 months) interaction for CSBS social composite score (F=10.0, p<0.0001), consistent with the previously reported unfolding of social deficits in HR-ASD subjects during the second year of life [10]. This finding was further illustrated by the observation that CSBS effect size almost tripled from 12 (d=0.39) to 24 (d=1.22) months.

Predicting Diagnosis of ASD at 24 Months from Selected Brain Measures in the First Year Based on earlier findings from our group on surface area, cortical thickness and brain volume [6], we sought to examine the utility of selected MRI brain measurements at 6 and 12 months of age to accurately identify those infants who will meet criteria for ASD at 24 months of age. Therefore, independent of the results of the above analyses, a machine learning classification algorithm based on a deep learning network [22] was employed to investigate how well regional SA and CT at 6 and 12 months, ICV, and gender were at predicting HR-ASD diagnosis at 24 months of age. Only infants with CT and SA data from both 6 and 12 months were included. A ten-fold cross-validation was employed to compute classification performance, where the whole classification procedure including network training was performed separately in each fold.

FIG. 3 depicts a table containing information about a prediction model using cortical data to classify groups at 24 months. In FIG. 3, information is provided about a non-linear prediction model. The non-linear prediction model included the following unbiased/unweighted information: sex, age corrected ICV, and age-corrected SA and CT measurements from 39 left and 39 right cortical hemisphere regions at 6 months and 12 months. The prediction model was evaluated using a standard ten-fold cross validation approach. Classification performance of the prediction model is at 94% overall accuracy, 88% sensitivity, 95% specificity, 81% positive predictive value and 97% negative prediction value.

The classification scheme distinguished the HR-ASD group from the HR-neg group in the cross-validation with 88% (N=30/34) sensitivity, 95% (N=138/145) specificity, 81% (N=30/37) positive predictive value (PPV), and 97% (N=138/142) negative predictive value (NPV)) (FIG. 3). Additional inspection of the trained deep learning networks indicate that SA seems more important than CT to the discrimination as 11 of the top 12 measures contributing to the deep learning network are regional SA measures.

Discussion

In the study associated with the present specification, brain volume overgrowth between 12 and 24 months in infants with ASD is documented. Longitudinal trajectories for this group differed from those high risk and low risk infants who did not develop ASD. Cross-sectional volume differences not present at 6 or 12 months appeared during the 12-24 month interval. Overgrowth appeared to be generalized throughout the cortex. Overgrowth during the second year was linked to severity of autistic social behavior at 24 months at a time when the emergence of social deficits was observed in the HR-ASD infants. The temporal link between the timing of brain overgrowth and emergence of social deficits suggests that brain overgrowth may play a role in the development of autistic social behaviors.

Our data implicate very early, post-natal hyper-expansion of cortical surface areas as playing an important role in the development of autism. Rate of cortical surface area expansion from 6 to 12 months was significantly increased in individuals with autism, and was linked to subsequent brain overgrowth. This suggests a sequence whereby hyper-expansion of cortical surface area is an early event in a cascade leading to brain overgrowth and emerging autistic deficits. In infants with autism, surface area hyper-expansion in the first year was observed in cortical areas linked to processing sensory information (e.g., left middle occipital cortex), consistent with regions previously reported to have the earliest increase in SA growth rate in the typically developing infant [24], and with reports showing early sensory and motor differences in infants later developing ASD [25-28].

The finding of brain overgrowth in this sample of young children with 'idiopathic' ASD is consistent with an emerging literature demonstrating brain overgrowth in genetically-defined ASD subgroups (e.g., 16p11 deletions [29], Pten [30] and CHD8 [31]). Cellular mechanisms and heritability underlying SA expansion are thought to differ from mechanisms underlying cortical thickness [32-34], and SA hyper-expansion has been reported in genetically-engineered mouse models of autism [35, 36]. The findings from this report are consistent with the mini-column hypothesis of autism [37] suggesting that symmetrical proliferation of periventricular progenitor cells, leading to an increased number of mini-columns, may have a role in the pathogenesis of SA hyper-expansion and later emergence of the disorder [34, 38], although other mechanisms of post-natal growth (e.g., dendritic arborization and decreased pruning) must also be considered. A report by Fan et al., [39] suggested that overproduction of upper-layer neurons in the neocortex leads to autism-like features in mice, while the 16p11.2 deletion mouse has been shown to exhibit altered cortical progenitor proliferation [40]. Building on this hypothesis, a recent imaging study described the presence of increased brain volume in individuals with 16p11 deletion, a genetically-defined subgroup of individuals with 'syndromic autism' [28]. Regulation of cerebral volume has been linked to expansion of basal progenitor cells in rodent models [41] and genetically engineered mouse models involving ASD-associated genes (e.g., CHD8) suggest dysregulation of neural progenitor cell proliferation as well as other diverse functions [42]. Recent work by Cotney et al. [43], demonstrates the importance of CHD8 mediated regulatory control and suggests the potential role in cell cycle pathways involved in proliferation of neurons during early human brain development. Understanding the mechanisms underlying surface area hyper-expansion in the first year in human infants is likely to provide important insights into the pathogenesis of autism.

Prediction models developed from behaviorally-based algorithms during infancy have not provided sufficient predictive power to be clinically useful [44-47]. We found that a deep learning algorithm primarily using surface area information from brain MRI at 6 and 12 months of age accurately predicts the 24 month diagnosis of autism in 94% of ASD-positive children at high risk for autism. This finding has important implications for early detection and intervention, given that this period is prior to the common age for diagnosis of autism [48]. The early part of the second year of life is characterized by greater neural plasticity relative to later ages and is a time when autistic social deficits are not yet well established. Intervention at this age may prove more efficacious than later in development. The fact that we demonstrate group differences in surface area growth rate from 6-12 months, that very early surface changes are linked to later brain overgrowth in the second year, and that overgrowth is, in turn, linked to the emergence of core social deficits in autism during this period, provides additional context to support the validity of the prediction model we report. The positive predictive value findings from this high risk study are probably conservative in nature due to the likelihood that our HR-ASD group is milder than those who are clinically-referred and diagnosed with ASD at 24 months of age, and that HR-Neg groups are known to be more heterogeneous with respect to later development of cognitive, behavioral, social-communication and motor deficits than typical case control studies [49]. Our estimated PPV would therefore differ in other populations, such as community ascertained clinical samples.

Our approach may require replication before being considered a clinical tool for predicting ASD in high risk infants, as false diagnostic predictions have the potential to adversely impact individuals and families. We do not know, for example, how this method would perform with other disorders (e.g., fragile X, intellectual disability) and whether the brain differences we see are specific to autism or share characteristics with other neurodevelopmental disorders. However, if confirmed, this finding may have clinical utility in families with high familial risk infants so that those infants identified could begin intervention as early as possible. While the findings of this study do not have direct clinical application to the larger population of children with ASD who are not known to be at high familial risk for ASD, these findings provide a proof-of-principle, suggesting that early prodromal detection is possible. Conducting prediction studies using biomarkers is not yet a practical tool for the general population. Future studies can begin to search for more cost-effective, surrogate biomarkers that can be used in those outside of the high familial risk group, as well as in high familial risk families. Future analyses incorporating complementary data from other relevant modalities (e.g., behavior and other imaging metrics) may improve the accuracy of the prediction we observed, adding to the clinical utility of early prediction models for autism.

In interpreting the findings from this study there are additional limitations worthy of note. First, diagnostic classification in a small but significant number of infants classified with and without ASD at 24 months may change as children mature, although the reason for this change is not well understood (i.e., whether it reflects the natural history of the condition in a subset of children, misclassification at 24 months, or is the effect of some unknown intervention operating in the local environment). However, potential later classification changes do not diminish the importance of recognizing a diagnosis of ASD at 24 months of age. Second, difficulties with gray-white segmentation on MRI at 6 months are well known. In the future better segmentation methods may improve on the current findings. Although the largest brain imaging study to date during this time interval, given the heterogeneity of autism, the sample size should still be considered modest.

Methods

Sample

This study includes data acquired from an NIH-funded Autism Center of Excellence (ACE) network study, called the Infant Brain Imaging Study (IBIS). The network includes four clinical data collection sites (University of North Carolina at Chapel Hill, University of Washington, Children's Hospital of Philadelphia, Washington University in St. Louis), a Data Coordinating Center at the Montreal Neurological Institute (McGill University), and two image processing sites (University of Utah and UNC). Data collection sites had approved study protocols by their Institutional Review Boards (IRB) and all enrolled subjects had informed consent (provided by parent/guardian). Infants at high-risk for autism (HR) and typically developing infants at low risk (LR) entered the study at 6 months of age (some HR were allowed to enter at 12 months) and seen for follow-up assessments at 12 and 24 months. Results from the 6 month brain volume findings have previously been reported [50].

Subjects were enrolled as HR if they had an older sibling with a clinical diagnosis of an ASD and confirmed by an Autism Diagnostic Interview [51](ADI-R). Subjects were enrolled in the LR group if they had an older sibling without evidence of ASD and no family history of a first or second-degree relative with ASD. Exclusion criteria for both groups included the following: (1) diagnosis or physical signs strongly suggestive of a genetic condition or syndrome (e.g., fragile X syndrome) reported to be associated with ASDs, (2) a significant medical or neurological condition affecting growth, development or cognition (e.g., CNS infection, seizure disorder, congenital heart disease), (3) sensory impairment such as vision or hearing loss, (4) low birth weight (<2000 grams) or prematurity (<36 weeks gestation), (5) possible perinatal brain injury from exposure to in-utero exogenous compounds reported to likely affect the brain adversely in at least some individuals (e.g., alcohol, selected prescription medications), (6) non-English speaking families, (7) contraindication for MRI (e.g., metal implants), (8) adopted subjects, and (9) a family history of intellectual disability, psychosis, schizophrenia or bipolar disorder in a first-degree relative. The sample for this analysis included all children with longitudinal imaging data processed thru Aug. 31, 2015. The final sample included 319 HR and 120 LR children each with 2-3 MRI scans.

Children in the HR group were then classified as HR-ASD if, at 24 months of age, they met DSM-IV-TR criteria for either Autistic Disorder or PDD-NOS, by an expert clinician (blind to the imaging data). HR subjects were classified as HR-neg (i.e., negative for autism) if they failed to meet criteria on the DSM-IV-TR for ASD or PPD-NOS. The rationale for this conservative approach was to maximize certainty of diagnosis at 24 months of age [52]. LR subjects did not meet ASD criteria on the DSM-IV-TR clinical best estimate assessment. Three LR who met criteria for ASD at 24 months were excluded (see Supplementary Information for more details). There is strong evidence of differences in the underlying genetic architecture of multiple versus single incidence (or sporadic) cases, with the later often being attributed to de novo events, that support our exclusion of these subjects from a combined analysis with the HR-ASD subject group, who are HR infant siblings. The final HR groups included 15 HR-ASD and 91 HR-neg, with 42 children in the LR group.

Assessment Protocols

Behavioral assessment: Infants were assessed at ages 6, 12 and 24 months and received a brain MRI scan in addition to a battery of behavioral and developmental tests. The battery included measures of cognitive development, adaptive functioning, and behaviors associated with autism. Developmental level and adaptive functioning were assessed at each time point using the Mullen Scales of Early Learning [13] and Vineland Scales of Adaptive Behavior [14]. Autism-oriented assessments included the Autism Diagnostic Observation Scale [17] (ADOS-WPS) at 24 months and Communication and Symbolic Behavior Scales of Development Profile [20](CSBS-DP) at 12 and 24 months. From the CSBS, the total raw score and the social composite raw score were used in the brain-behavioral analyses. Raw scores were used to allow for better representation of the distribution of the data.

MRI acquisition: The brain MRI scans were completed on 3T Siemens Tim Trio scanners with 12-channel head coils and obtained while infants were naturally sleeping. The imaging protocol included (1) a localizer scan, (2) 3D T1 MPRAGE: TR=2400 ms, TE=3.16 ms, 160 sagittal slices, FOV=256, voxel size=1 mm [3], (3) 3D T2 FSE TR=3200 ms, TE=499 ms, 160 sagittal slices, FOV=256, voxel size=1 mm [3], and (4) a 25 direction DTI: TR=12800 ms, TE=102 ms, slice thickness=2 mm isotropic, variable b value=maximum of 1000 s/mm [2,], FOV=190.

A number of quality control procedures were employed to assess scanner stability and reliability across sites, time, and procedures. Geometry phantoms were scanned monthly and human phantoms (two adult subjects) were scanned annually to monitor scanner stability at each site across the study period. Details on the stability procedures for IBIS and scanner quality control checks are described elsewhere [50].

Radiologic Review. All scans were reviewed locally by a pediatric neuroradiologist for radiologic findings that, if present, were communicated to the participant. In addition, a board certified pediatric neuroradiologist (R.C.M., Washington University) blindly reviewed all MRI scans across the IBIS network and rated the incidental findings. A third neuroradiologist (D.W.W.S., University of Washington) provided a second blind review for the Washington University site, and contributed to a final consensus rating if there were discrepancies between the local site reviews and the network review. The final consensus review was used to evaluate whether there were group differences in the number and/or type of incidental findings. Scans were rated as either normal, abnormal, or with incidental findings. No scans rated as abnormal were included in the analysis, and previous examinations of our data did not find group differences in incidental findings [50]. Scans rated as clinically abnormal by a site pediatric neuroradiologist (and independently confirmed by two study pediatric neuroradiologists) were excluded (N=3).

Image Processing

Image processing was performed to obtain global brain tissue volumes, regional brain tissue volumes, and cortical surface measures. All image processing was conducted blind to the subject group and diagnostic information. The brain volumes were obtained using a framework of atlas-moderated expectation-maximization including co-registration of multi-modal (T1w/T2w) MRI, bias correction, brain stripping, noise reduction, and multivariate classification with the AutoSeg toolkit [53](http://www.nitrc.org/projects/autoseg/). Population average templates and corresponding probabilistic brain tissue priors, for white matter (WM), gray matter (GM), and cerebrospinal fluid (CSF) were constructed for the 6 to 24 month old brain. The following brain volumes were generated at all ages: intracranial volume (ICV), total brain volume=gray matter (GM) plus white matter (WM), total cerebrospinal fluid (CSF), cerebrum, cerebellum, and lateral ventricles. ICV was defined as the sum of WM, GM, and CSF. Total brain tissue volume (TBV) was defined as the sum of WM and GM. Subjects were included in the volumetric analyses if they had successfully segmented scans at 6, 12, and 24 months and corresponding body length measures. Image processing may involve a pipeline that includes the following steps:

A) Initial Preprocessing Steps
  1. Rigid body co-registration of both T1w and T2w data to a prior atlas template in pediatric MNI-space generated from 66 one-year old subjects from this study (see Kim et al [65] for more detail).
2. Correction of intensity inhomogeneity via N4 [66]
3. Correction of geometric distortions for optimal processing of multi-site longitudinal data [67]

B) Tissue Segmentation

Brain volumes were then obtained using a framework of atlas-moderated expectation-maximization that performs the following steps (see Kim et al [65] or more detail):
1. Co-registration of T2w data to T1w data
2. Deformable registration of a prior template and propagation of prior tissue probability maps for white matter (WM), gray matter (GM), and cerebrospinal fluid (CSF) from MNI space into individual T1w data. The template images are population averages computed at 6, 12 and 24 months of age [68]
3. For 12 month old data only: T1w and T2w intensities were locally adapted using a prior intensity growth map that quantifies the expected change in intensity from 1 to 2 years of age [65]
4. Expectation Maximization based tissue segmentation including parametric intensity inhomogeneity correction [65]
5. Brain masking was performed using the tissue segmentation as masking. If necessary, manual correction of the brain masks were performed.

Steps 1-5 were computed using the AutoSeg toolkit (http://www.nitrc.org/projects/autoseg/). ICV was defined as the sum of WM, GM, and CSF. Total brain tissue volume (TBV) was defined as the sum of WM and GM. Segmentation of 6 month old data did not yield reliable separation of WM and GM, and thus no individual analysis of either was performed here.

C) Cortical Surface Measures

Cortical thickness (CT) and surface area (SA) measures for 12 and 24 month data were obtained via a CIVET workflow [54, 55] adapted for this age using an age corrected automated anatomical labeling (AAL) atlas [56]. CIVET includes shrink-wrap deformable surface evolution of WM, local Laplacian distance and local SA, mapping to spherical domain, co-registration using cortical sulcal features and extraction of regional measurements via a deformably co-registered fine-scale lobar parcellation. SA was measured at the mid-cortical surface. CT and SA measures for 6 month data were extracted from surfaces propagated via deformable multi-modal, within-subject, co-registration [57] of MRI data at 12 months.

CIVET was applied as described above to 12 month and 24 month data following tissue segmentation with AutoSeg (step B).

For 6 month old datasets: As tissue segmentation (step B) for 6 month old subjects did not yield reliable white vs. gray matter segmentations, cortical surfaces at 6 months were determined longitudinally, only for subjects with MRI data at both 6 month and 12 month visits. Using ANTs deformable diffeomorphic symmetric registration with normalized cross correlation (metric radius 2 mm, Gaussian smoothing of 3 mm of the deformation map) of joint T1w and T2w data (both image sources were equally weighted), the pre-processed, brain masked MRI data of 12 month old subjects was registered to data from the same subject at age 6 months. This registration was applied to the cortical surfaces of the 12 month subjects to propagate them into the 6 month old space. Surfaces at 6 months were then visually quality controlled with surface cut overlay on the MRI images. Local SA and CT measures at 6 month were finally extracted from these propagated surfaces.

Regional measures: Thickness measurements were averaged for all vertices within each of the 78 brain regions in the AAL label atlas. The surface area measurements were summed over all vertices of each AAL region for a total regional surface area.

Statistical Analysis

A random coefficient 2-stage piecewise mixed model was used as a coherent framework to model brain growth trajectories in the first and second year and test for group differences. As reported by Knickmeyer [61] on brain growth in the first two years, the brain growth is faster in the first year than the second year. The two-stage piecewise model was chosen to capture the change in growth rate among subjects with scans at 6, 12 and 24 months. The modeling strategy was applied to brain volume, surface area and cortical thickness outcomes.

The brain growth was modeled in relativity to normative body growth in the first two years when normative age based on body length was used instead of chronological age. Body length highly correlates with chronological age while taking into account the infant's body size, which is necessary to determine the relative brain overgrowth. In order to account for sex-related body size differences and their effects on brain volume [58-60], we normalized differences in body size by using the sex-specific WHO height norms. The normative age for each infant's body size (estimated from length as calculated by WHO Child Growth Standards) was used in the model as the continuous growth variable.

As a multi-site study, site and sex are used as covariates for the model. Even with regular calibration cross sites, the site covariate was included to account for both cohort differences and potential administrative differences. We have also included sex as a covariate in the analysis model to account for any remaining sex-related differences not accounted by sex-specific normative age.

The association of 24 month clinical outcome with brain growth rates from 6-12 and 12-24 month intervals was assessed among HR subjects using Pearson correlation. Family income, mother's education, subject sex, and birth weight were examined as potential covariates, but none contributed significantly and were excluded from the final analysis.

The machine learning analysis used a non-linear prediction model based on a standard three-stage deep learning network and included the following unbiased/unweighted information: sex, age-corrected ICV, and age-corrected SA and CT measurements from 39 left and 39 right cortical hemisphere regions at 6 months and 12 months (approximately 312 measurements). The model was evaluated via a standard ten-fold cross-validation. The core of the prediction model is a weighted three-stage neural/deep learning network [22], where the first stage reduces 315 measures to 100, the second stage reduces 100 to 10, and the third stage reduces 10 to only 2 such measures. At each stage, the measures (in the progressively smaller sets) are the weighted combination of input measures from the previous stage. In general, the training process determines a) those network weights that retain information that is associated with the optimal reconstruction of data when inverting the network (so-called auto-encoding), as well as b) the linear support vector machine based classification decision that separates the group label (HR-ASD and HR-neg) in the two dimensional final network space. Thus to apply the prediction model, the data is first inserted into the two dimension final network space using the trained deep learning network, and then classified in the final network space using the trained support vector machine. All training was performed purely on the training data in each fold. Once training was achieved, this prediction model was applied to the testing data in each fold. Classification measures of sensitivity, specificity, positive and negative predictive value are combined and reported across the 10 folds.

Machine Learning Analysis

1. Rationale for Non-Linear Classification

Children with autism show an abnormal brain growth trajectory that includes a period of early overgrowth that occurs within the first year of life. In particular, the total size of the brain is up to 10 percent larger in children with autism than typically developing children [73]. Thus the brain of a child with autism will typically show larger morphological differences such as intra-cranial cortical volume, cortical surface area, and cortical thickness. To estimate these growth trajectories, or growth patterns, linear models [73]' [74] have been applied, however these are primarily concerned with changes in total volume and not specific regions in the brain, or how the growth patterns in specific brain regions may differentiate typically developing children with autism. Also, as suggested by Giedd, [75] linear models may not accurately represent complex (i.e. non-linear) growth patterns in the developing brain. As a result, classification methods that use linear models to recognize these complex brain growth patterns may not be the most suitable choice.

Recently, deep learning (DL) [76]' [77]' [78] has been used to estimate low dimension codes (LDC) that are capable of encoding latent, non-linear relationships in high dimension data. Unlike linear models such as PCA, kernel SVM, local linear embedding, and sparse coding, the general concept of deep learning is to learn highly compact hierarchical feature representations by inferring simple ones first and then progressively building up more complex ones from the previous level. To better understand these complex brain growth patterns within the first year of life, DL is a natural choice because the hierarchical deep architecture is able to infer complex non-linear relationships, and the trained network can quickly and efficiently compute the low dimension code for newly created brain growth data.

2. Methods and Materials 2.1 High Dimension Feature Vector

Each child in the training and test populations is represented by a d=315 dimension feature vector that includes longitudinal cortical surface area (CSA), cortical thickness (CTH), intra-cranial volume (ICV) real-valued morphological measurements, and one binary gender feature (sex Male or Female). Specifically, features 1-78 are CSA measurements at 6 months, and features 79-156 are CSA measurements at 12 months. Each measurement corresponds to a brain region defined in the AAL atlas. Likewise, features 157-234 are CTH measurements at 6 months, and features 235-312 are CTH measurements at 12 months. Lastly, features 313 and 314 correspond to ICV measurements at 6 and 12 months respectively, and feature 315 is the sex of the subject.

Lastly, because the infant brain develops so quickly within the first year of life, to adjust for differences in the actual age at acquisition for the 6 month and 12 month visit (i.e. the "6 month" image acquisition of a subject does not exactly occurs at 6.0 months, but rather at, e.g., 5.7 or 6.2 months), all morphological measurements in the 315 dimensional feature vector are linearly age-normalized. Specifically, the 6-month CSA, CTH, and ICV measures are multiplied by $\Delta_{6M}=6/\alpha_{6M}$, where $\alpha_{6M}$ is the subject's actual age at "6 month" image acquisition. And the 12-month CSA, CTH, and ICV measures are multiplied by $\Delta_{12M}=2/\alpha_{12M}$, where $\alpha_{12M}$ is the subject's actual age at the "12 month" image acquisition.

2.2 Prediction Pipeline

Figure 8:
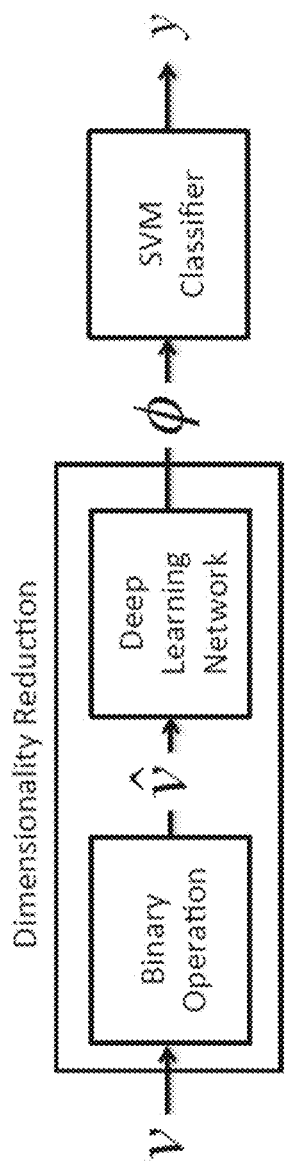
FIG. 8 is a block diagram illustrating a two-stage prediction pipeline that includes a non-linear dimension reduction step followed by a SVM classification step.

To better recognize brain overgrowth patterns in autistic children within the first year of life the proposed prediction pipeline uses the 2-stage design illustrated in FIG. 8 to recognize complex morphological patterns in different brain regions that are likely to differentiate children with autism from typically developing children. The prediction pipeline in FIG. 8 includes a DL based dimensionality reduction stage followed by a SVM classification stage. In general, the chosen two-stage design is a very common configuration (low dimension feature representation stage followed by a classification stage), and has been used in several state-of-the-art pipeline designs [80]' [81]' [82]' [83]' [84] that only use DL to approximate a new lower dimension feature representations, or LDC representations in our case, that are then used to train a separate classifier. To ensure the trained two-stage pipeline had optimal classification performance, a median DL network N is constructed using only those trained DL networks that resulted in a two-stage pipeline with PPV and accuracy scores ≥90% as measured on the training data only.

In general, the prediction pipeline is applied as follows (assuming that the prediction pipeline has been trained): First, given a high dimension feature vector v not included in the training data set, the real-valued vector is transformed into a binary feature vector $\hat{v}$ using a trained binary masking operation, then the low dimensional code (LDC) $\phi$ is estimated using a trained DL network. Next the diagnosis label y for $\phi$ is found using a trained SVM classifier. The technical details of each stage are outlined below.

The decision to implement a 2-stage prediction pipeline was primarily driven by two different design considerations: 1) creation of a self-contained non-linear dimensionality reduction algorithm that did not incorporate a classification mechanism, and 2) a flexible design where different classification algorithms, such as a support vector machines or distance weighted discrimination (DWD) classifiers, can be applied with little to no effort.

It is noteworthy that the dimensionality reduction stage in the proposed pipeline could be reconfigured to become a deep classification network.

Non-Linear Dimensionality Reduction

Given a n×d training data matrix $A=\{a_1, a_1, \ldots, a_i, \ldots a_n\}$ of n subjects where row vector $a_i=(a_{i1}, \ldots, a_{id})$ represents the high dimension feature vector for subject i, and $y=(y_1, y_2, \ldots, y_n)$ is a dimension vector that defines the binary group label for each subject in the training data set (i.e. the paired diagnosis information for row vector $a_i$ is $y_i$, 0=HR-ASD and 1=HR-neg in our study), a binary operation $f: \mathbb{R}^d \to \{0,1\}^d$ is first applied to transform the each real-valued measurement $a_{jd}$, into a binary one. Specifically, for each column vector $a_j$, $j=1, \ldots, d$ in A, an average median threshold $m_j=(m_j^{l_0}+m_j^{l_2})/2$ is calculated where $m_j^{l_0}$ is the median value of feature j and diagnosis label $l_0$, and $m_j^{l_2}$ is the median value of feature j and diagnosis label $l_1$. Values in $a_j$ that are less than or equal to $m_j$ are set to 0, and those that are greater than $m_j$ are set to 1.

Even though more sophisticated binary operations, such as local binary patterns (LBP), exist they are typically used in DL networks that attempt to classify gray-level texture patterns representing local image patches [85]' [86]. In our case, our features are not image patches, so the LBP approach is not appropriate for application. Furthermore, it is very common to perform an unsupervised training procedure on individual two-layer greedy networks (such as restricted Boltzman machines and auto-encoders) using visible layer features that are binary and not real-valued [76]' [83]. In fact, there is evidence (suggested by Tijmen Tieleman), that when binary features are used in the visible layer this may reduce sampling noise that allows for fast learning [87]. Lastly, the strategy behind the binary operation chosen for this application is directly related to the overgrowth hypothesis. More specifically, we are not interested in finding growth patterns that are precisely tied to an exact surface area or thickness measurement; we are more interested in something that is posed a binary question "binary" question. That is, is the value of this feature greater than a median value (possible overgrowth is true), or less than median value (possible overgrowth is false)? This approach allows us to train the DL network using simple binary patterns instead of complex real-valued ones; as a result the binary operation may allow us to faster train the DL network (i.e. faster convergence), and as the reported results show, even though we may loose some information when the binary operation is applied, the prediction performance of the two-stage pipeline speaks for itself.

When the binary operation completes a new training population $\hat{A}=\{\hat{a}_1, \hat{a}_1, \ldots, \hat{a}_n\}$ is created where each binary high dimension feature vector now describes inter-subject brain region (cortical surface area and thickness) growth patterns, and inter-subject ICV growth patterns.

Next, the binary high dimension features in  are used to train a deep network that is implemented using the publically available deep learning Matlab toolbox called Deep-Learn Toolbox (found at https://github.com/rasmusbergpalm/DeepLearnToolbox). In general, the deep network is trained by performing the two sequential steps listed below.

Figure 9:
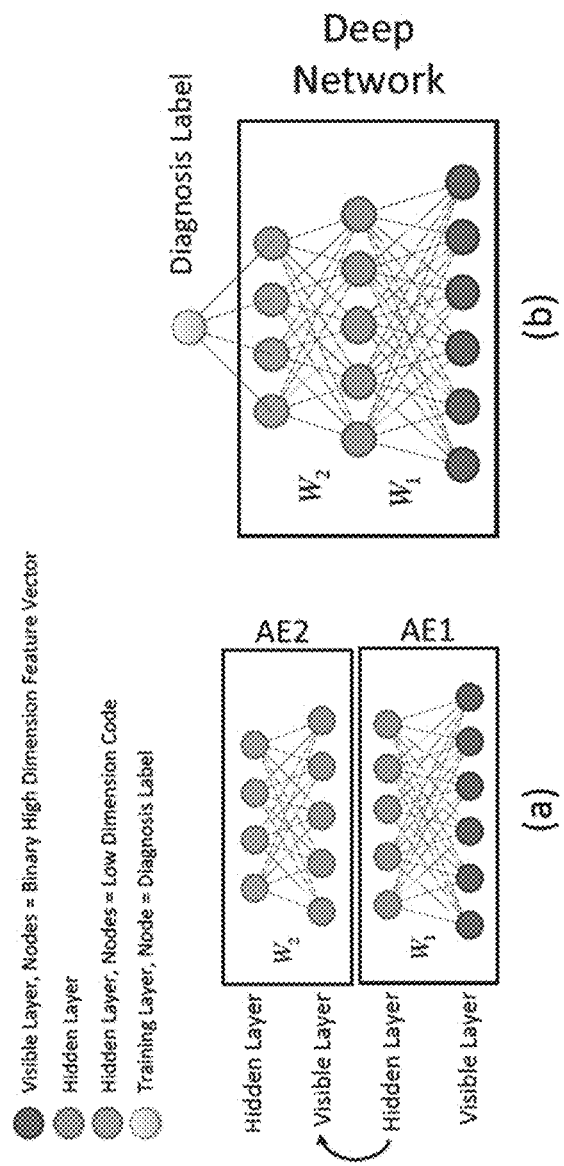
FIG. 9 illustrates various layers within an example deep learning network.

FIG. 4 provides a visualization of the various layers within the deep network. Within each node is a visible layer and a hidden layer. Each combine to form a network layer and ultimately provide a diagnostic label. As illustrated in FIG. 9(a), an unsupervised step is first performed that sequentially trains individual autoencoders (AE). In particular, an AE is a 2-layer bipartite graph that has a visible layer (input) and hidden layer (output). Initially, the edge weights (represented by a matrix w) in the bipartite graph are randomly chosen, and then iteratively refined [76] (including a set of bias values) using data step $$h = Wv + \beta_d$$

followed by a reconstruction step $$\tilde{v} = W^t h + \beta_r$$

where vector v represents the nodes in the visible layer, vector h represents the nodes hidden layer, vectors $\beta_d$ and $\beta_r$ represent the bias values for the data and reconstruction steps, vector $\tilde{v}$ represents the reconstructed nodes in the visible layer, and $\sigma(\bullet)$ is the sigmoid function. In general, the AE convergence criteria is:

The maximum number of epochs is reached (that is set to 100), or

The average mean square error (MSE), $MSE_e = 1/\delta \sum_{i=1}^{\delta} (\tilde{v}_i^s - \tilde{v}_i^{s-1})^2$ for the last 10 consecutive epoch (i.e., e=1, 2 ... 10) is less than 0.01, where $\tilde{v}_i^e$ is the reconstructed visible layer at epoch e, and $\tilde{v}_i^{e-1}$ is reconstructed visible layer at epoch e-1.

Figure 10:
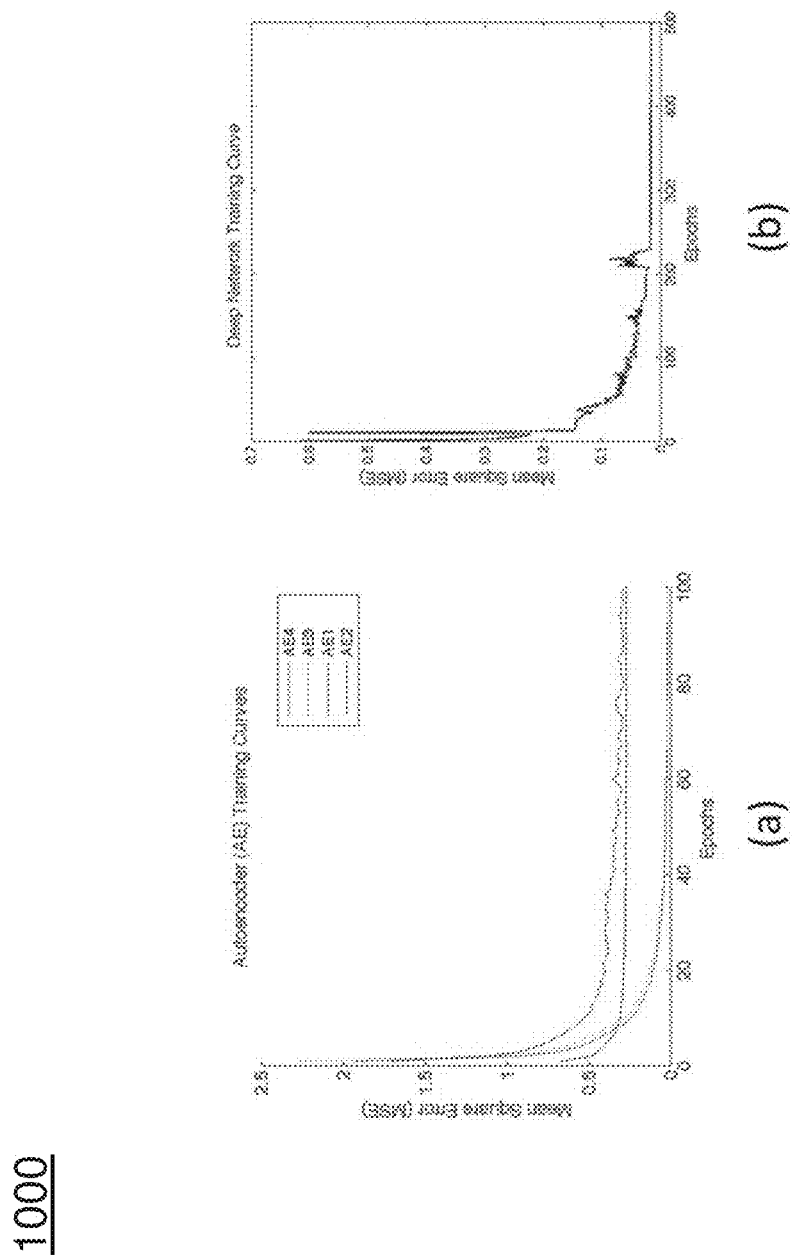
FIG. 10 shows training performance in an example deep learning network.

FIG. 10 shows an example training performance (as measured by the mean square error) for (a) the autoencoding step (step 1 of the deep network training) with separate curves for the 4 layers in the network, and (b) for the supervised training step (step 2). FIG. 10(a) shows a typical training curve for each AE in the proposed 4-layer architecture. When the AE training step terminates and the hidden layer in current AE becomes the visible layer in the next AE, and the unsupervised process repeats itself for each AE in the deep network. In general, the goal of the unsupervised step is to approximate edge weight and bias values that increase the likelihood of finding the global optimum, or at least a very good local minimum, during the supervised step.

As illustrated in FIG. 9(b), the supervised step stacks the initialized AEs (i.e. creating the deep network) and then adds one additional layer for the supervised training only (i.e. training label layer) that contains the binary diagnosis label for each binary high dimension feature vector in the training population. At this point the deep network is treated as a traditional feed forward neural network that uses back propagation to fine-tune the initial weight values in each AE (see FIG. 10(b) for a typical training curve at this stage). Once the supervised step completes, the training label layer is removed, and the number of nodes in last hidden layer represents the final dimension of the output LDC.

Figure 11:
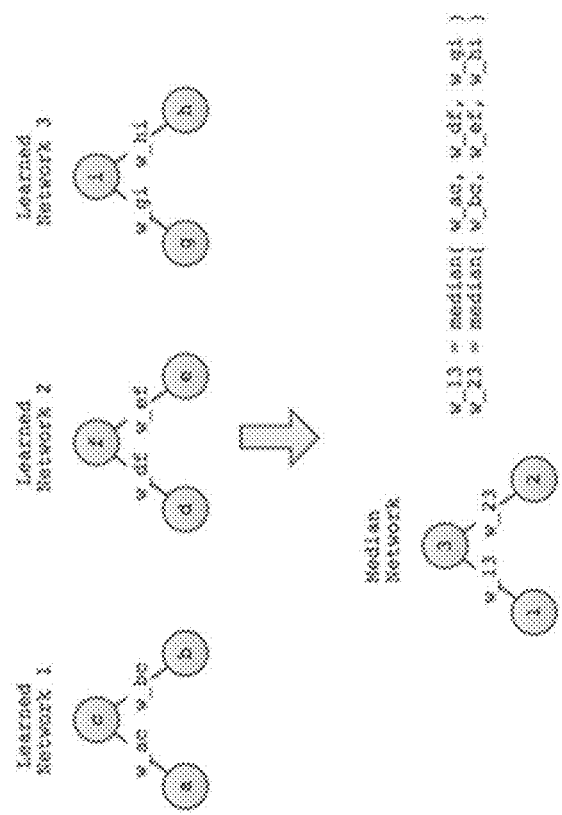
FIG. 11 illustrates how each of the edge weights may be calculated in an example deep learning network.

Since the initial edge weights in unsupervised step are randomly chosen, it is likely that the result of the training procedure depends on that random initialization. To mitigate this problem the deep network procedure was performed with 10,000 random initializations resulting in a set of fine-tuned networks $\{N_1, N_2, \ldots, N_{10,000}\}$ (all trained with the same training set). Using the edge weight matrices and bias values in each fine-tuned network in $\{N_1, N_2, \ldots, N_{10,000}\}$, an initial median network is constructed. The median calculation is illustrated in FIG. 11 using a simple two-layer network that only defines three nodes (note: w_ac represents the edge weight that connects node a and node c). FIG. 11 illustrates how each of the edge weights may be calculated in the DL network.

Once the initial median network is constructed, the edge weight and bias values are further refined by one additional, final supervised training step. That is, the median weights become the initial weights (i.e. starting weights for back propagation optimization), thus giving us a potentially more robust starting point for the supervised training step that may lead to a fine-tuned deep network that is highly reproducible. Finally, the fully trained median deep network $\overline{N} = \{\{\overline{W}_1, \overline{\beta}_1\}, \{\overline{W}_2, \overline{\beta}_2\}, \ldots, \{\overline{W}_k, \overline{\beta}_k\}\}$ is then used to estimate a LDC $\phi_i$ for subject $\hat{a}_i$.

The deep learning parameters momentum and learning rate were set to 0.7 and 1.25 respectively, and a four-layer architecture [315 100 10 2] was used, where the first layer, or input layer represented by a binary high dimension feature vector, defines 315 nodes, second hidden layer defines 100 nodes (approximately 70% feature reduction), the third hidden layer defines 10 nodes (90% feature reduction), and the last layer, or output LDC layer, defines 2 nodes (80% feature reduction). These parameters were chosen initially as suggested in UTML TR 2010-003, A Practical Guide to Training Restricted Boltzmann Machines, Geoffrey Hinton, and then experimentally refined using only the training data.

SVM Classifier

The LDCs $\{\phi_i, i=1, \ldots, n\}$ generated by the trained deep learning network along with the binary training labels $\{y_i, i=1, \ldots, n\}$ are then used to train a two-class SVM classifier that uses a linear kernel. The SVM classifier was implemented using the SVM Matlab toolbox (found at http://www.mathworks.com/help/stats/support-vector-machines.html) that is based on well-known LIBSVM library.

Once the SVM classifier is trained, the clinical outcome of a high dimension feature vector, say $v=(v_1, \ldots, v_d)$ not in the training data set can be predicted using the sequence of steps outlined below.

1. Estimate binary high dimension feature vector $\hat{v}=(v_1 m_1, v_2 m_2, \ldots, v_d m_d)$, where $\{m_1, m_2, \ldots, m_d\}$ is the learned median threshold values for each feature defined in the high dimension feature vector.
2. Estimate the LDC $\phi=(\phi_1, \phi_2, \ldots, \phi_\psi)$ for $\hat{v}$ using the median deep network $\overline{N}$, where $\psi$ represents the number of nodes in the last hidden layer.
3. Calculate predicted diagnosis label $$y = \sum_{i=0}^{\psi} \alpha_i \kappa(\delta_i, \phi) + b$$

where $\alpha$ are the weights, $\delta$ are the support vectors, $\kappa(\cdot)$ is the inner product of the two vectors, and b is the bias that define the linear hyper-plane (decision boundary) learned by the SVM algorithm. The sign of the calculated prediction value (i.e. $y \geq 0$ or $v < 0$) determines which of the two diagnosis labels the subject has been assigned.

2.3 Using Trained HR-ASD/HR-Neg Pipeline to Predict LR Subjects

To further validate the prediction accuracy of the prediction, we trained an HR-ASD/HR-neg pipeline on all HR subjects and classified all low risk (LR) subjects (no LR subjects were included in the training data set). In general, for these subjects the diagnosis label predicted by the HR-ASD/HR-neg pipeline should be HR-neg.

To be precise, we first describe here the general process of computing SVM based diagnostic labels from a high dimension feature vector, $v=(v_1, \ldots, v_d)$ (not in the training data) using the sequence of steps outlined below.

1. Estimate binary high dimension feature vector $\hat{v}=(v_1 m_1, v_2 m_2, \ldots, v_d m_d)$, where $\{m_1, m_2, \ldots, m_d\}$ is the learned median threshold values for each feature defined in the high dimension feature vector.
2. Estimate the LDC $\phi=(\phi_1, \phi_2, \ldots, \phi_\psi)$ for $\hat{v}$ using the learned deep network $\overline{N}$, where $\psi$ represents the number of nodes in the last hidden layer ($\psi=2$ in our case).
3. Calculate predicted SVM diagnosis label $$y = \sum_{i=0}^{\psi} \alpha_i \kappa(\delta_i, \phi) + b$$

where $\alpha$ are the weights, $\delta$ are the support vectors, $\kappa(\cdot)$ is the inner product of the two vectors, and b is the bias that define the linear hyper-plane (decision boundary) learned by the SVM algorithm. The sign of the calculated prediction value (i.e. $y \geq 0$ or $y < 0$) determines which of the two diagnosis labels the subject has been assigned.

Figure 12:
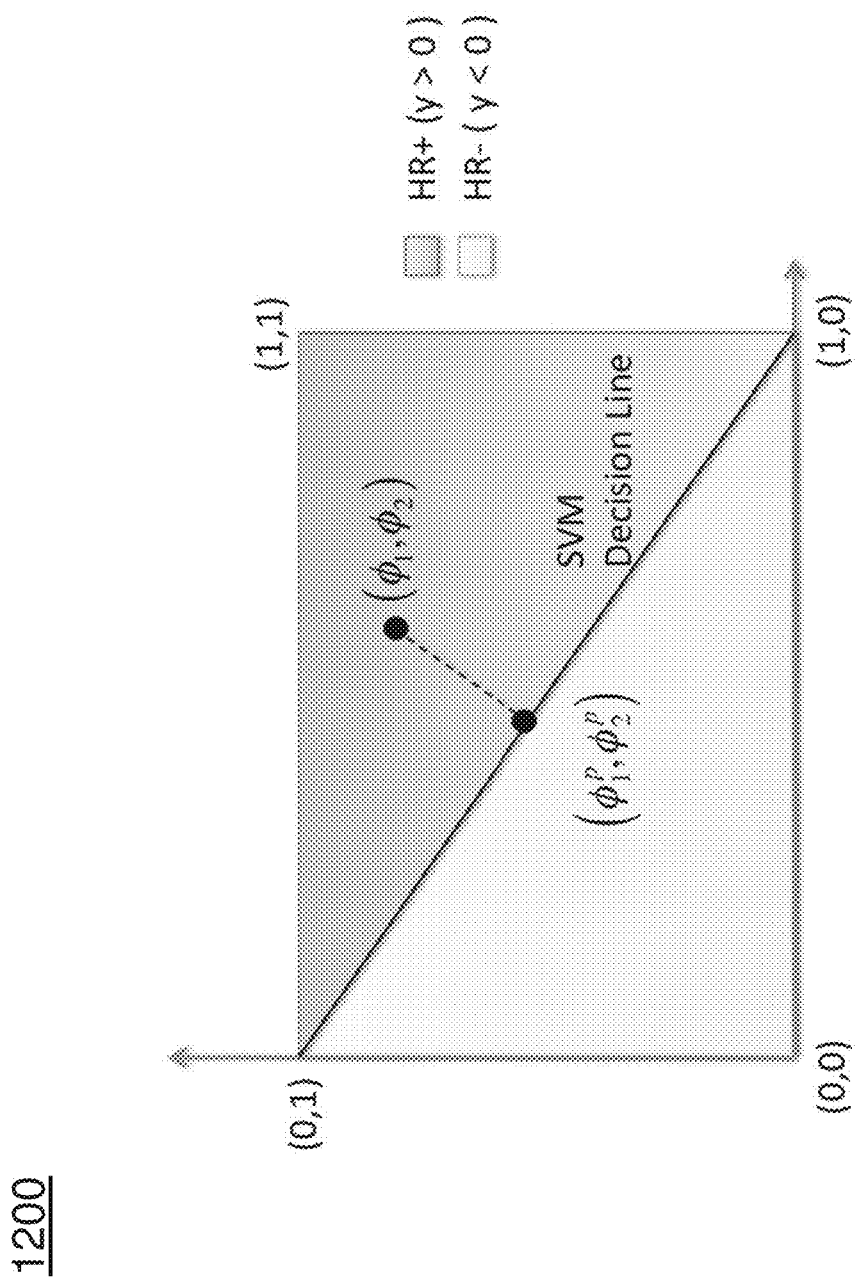
FIG. 12 illustrates the procedure to compute how far a subject is from a decision boundary.

Using the learned SVM parameters $\{\alpha, \beta, b\}$ that describe the linear decision boundary, we can now assess the strength or weakness of the prediction by the trained classification pipeline via the distance d to the SVM decision boundary, as schematically illustrated in FIG. 12 using an example 2D SVM decision space. FIG. 12 illustrates the computation of the distance to the decision boundary determined by the SVM classification step. The linear SVM separates the two-dimensional LDC space (output of the deep learning network) into two regions by a single decision line, one region for each class. The distance employed here to indicate whether a LR subject was safely or weakly classified is then simply the distance to that decision.

This distance d is computed using the following two steps:

Step 1: Take LR LDC $\phi=(\phi_1, \phi_2)$ and project $\phi^p=(\phi_1^p, \phi_2^p)$ onto into SVM decision line.
Step 2: Calculate the Euclidean distance $d(\phi, \phi^p)$ between two points using learned SVM decision parameters $\{\alpha, \delta, b\}$.

In general, the calculated distance can be interpreted as follows:

A distance close to zero would indicate a weak/unsure classification

A distance that is highly negative is a strong/safe classification for HR-neg

A distance that is highly positive is a strong/safe classification for HR-ASD

This analysis included 84 LR-subjects. No LR-ASD subjects with both available 6 and 12 mo surface area and cortical thickness data were available. Of the 84 LR subjects, 76 were classified (correctly) as HR-neg and 8 were classified (incorrectly) as HR-ASD. Some observations:

1. 90% (76/84) LR subjects were correctly classified as HR-neg
2. 10% (8/84) LR subjects were incorrectly classified as HR-ASD
3. 8% (7/84) LR subjects are (incorrectly) considered "safe" HR-ASD (at a distance higher than 0.15 from the decision boundary)
4. 7% (6/84) LR subjects are close to the decision boundary and thus are not considered clear decisions by our classification method (at a distance smaller than 0.15)
5. 84.5% (71/84) LR subjects are (correctly) considered safe HR-neg (at a distance higher than 0.15 from the decision boundary)
6. All of these subjects are not high-risk subjects and the prediction pipeline was purely trained for separating HR-neg from HR-ASD subjects.

2.4 Prediction Pipeline Cross-Validation Classification

The predictive power of the proposed two-stage HR-ASD/HR-neg pipeline is evaluated using a 10-fold cross-validation strategy. In particular, the HR-ASD and HR-neg subjects are first combined into one data set, and then partitioned into 10 different folds, where each fold contains high dimension feature vectors of randomly selected HR-ASD and HR-neg subjects. Furthermore, the ratio of HR-ASD to HR-neg subjects was maintained across each fold. The prediction pipeline (including the DL network generation) is fully re-trained in all its steps using the high dimension feature vector data in 9 of the 10 folds (i.e. a deep network was trained using 9 of the 10 folds) and then tested using the high dimension feature vector data in the remaining (or left out) fold. This iterative process terminates when each fold has been selected as the test one. Using the confusion matrix (TP=true positive, FP=false positive, FN=false negative, and TN=true negative) results in each test fold, the mean and standard error is reported for the specificity, sensitivity, positive predictive value, negative predictive value, and accuracy measures, where sensitivity (SEN)=TP/(TP+FN), specificity (SPE)=TN/(FP+TN), positive predictive value (PPV)=TP/(TP+FP), negative predictive value (NPV)=TN/(TN+FN), and accuracy (ACC)=(TP+TN)/(TP+FN+FP+TN). Table 300 in FIG. 3 shows the results of this cross-validation using the prediction pipeline described above.

Comparison with Other Classification Methods

For comparison purposes, using a smaller portion of the dataset (N=133), we compared the proposed two-stage prediction pipeline approach with 3 other approaches: 1) a traditional DBN that does not include a separate classification step, 2) two-stage approach that uses a linear a least squares linear regression algorithm (or sparse learning algorithm, SL) instead of a deep learning one, and 3) two-stage approach that uses principle component analysis (PCA) for dimensionality reduction.

Deep Classification Network

Figure 13:
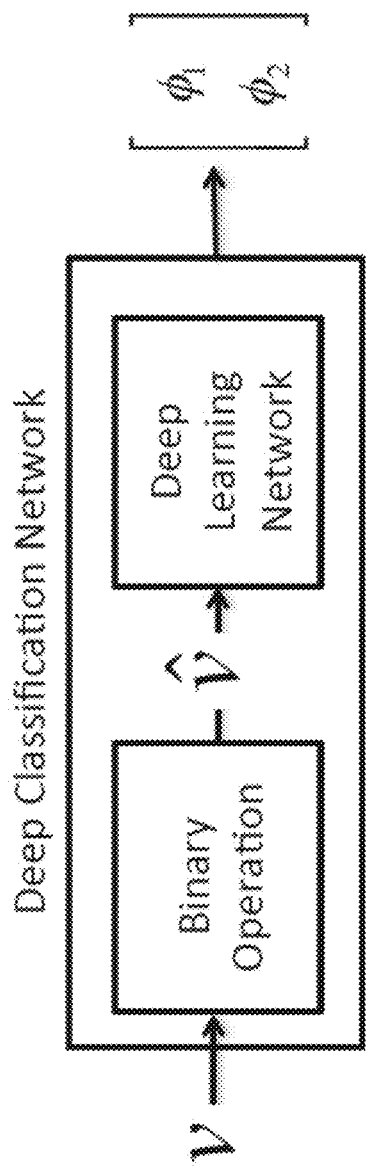
FIG. 13 is a block diagram illustrating a prediction pipeline reconfigured as a deep classification network.

It is noteworthy that the dimensionality reduction and the classification stages in the proposed pipeline could be combined into one stage creating a traditional deep classification network (DCN) as shown in FIG. 13. FIG. 13 demonstrates how the prediction pipeline is reconfigured to create a deep classification network. This network does not include a separate classification stage.

In the approach depicted in FIG. 13, the number of nodes in the last layer, i.e. $\phi_1$ and $\phi_2$ in the example DCN shown in FIG. 13, represent the diagnosis label (such as HR-ASD and HR-neg). Specifically, after the deep network is trained, an unknown high dimension feature vector is input into the deep network, and if the subject is HR-ASD then $\phi_1 > \phi_2$, otherwise the subject is ASD-neg. In this approach, the binary operation, deep learning parameters, and four-layer architecture outlined in the non-linear dimension reduction section was performed.

Sparse Learning and SVM Classifier

The elastic net algorithm [79] is used to find x a sparse weight vector that minimizes $$\min_x \frac{1}{2}\|Ax - y\| + \frac{\rho}{2}\|x\|_2^2 + \lambda\|x\|_1$$

where $\lambda\|x\|_1$ is the $l_1$ regularization (sparsity) term, $$\frac{\rho}{2}\|x\|_2^2$$

is the $l_2$ regularization (over-fitting) term. For this approach no binary operation is performed on matrix A, instead values are normalized as follows: $A(i,j)=(a_{ij}-\mu_j)/\sigma_j$ where $a_{ij}$ is the feature j for subject i, $\mu_j$ is the mean value for column vector j in matrix A, and $\sigma_j$ is the standard deviation for column vector j in matrix A. The above equation is optimized using the LeastR function in the Sparse Learning with Efficient Projections software package (found at http://www.public.asu.edu/~jye02/Software/SLEP). After optimization, x has weight values in [0 1] where 0 indicate network nodes that do not contribute to the clinical outcome, and weight values greater than zero indicate network nodes that do contribute to the clinical outcome. In general, x is referred to as the sparse representation of training data set. Lastly, in our approach each weight value in x greater than zero is set to one, therefore the resulting sparse representation is a binary mask, that is, the network node is turned on (value of 1) or turned off (value of 0). A new n×d sparse training matrix $\hat{A}=\{\hat{a}_1, \hat{a}_1, \ldots, \hat{a}_n\}$ is created, where row vector $\hat{a}_i=(a_{i1}x_1, a_{i2}x_2, \ldots, a_{id}x_d)$. Lastly, the row vectors in the newly created sparse training matrix by the along with the binary training labels $\{y_i, i=1, \ldots, n\}$ are then used to train a two-class linear kernel SVM classifier.

The sparse learning parameters $\lambda$ and $\rho$ were set to 0.5 and 1.0 respectively. In each fold, the sparse learning algorithm selected approximately 120 features from 315, which accounts for a 60% feature reduction. For all the reported results, a linear kernel SVM classifier was trained, and default parameters were used.

PCA and SVM Classifier

In order to further compare our results to standard Principal Component Analysis (PCA), we performed the following analysis:

1. For PCA no binary operation is performed on matrix A, yet normalization is still necessary. Input values are normalized as follows: $A(i,j)=(a_{ij}-\mu_j)/\sigma_j$ where $a_{ij}$ is the feature j for subject i, $\mu_j$ is the mean value for column vector j in matrix A, and $\sigma_j$ is the standard deviation for column vector j in matrix A.
2. Because there are fewer observations than features PCA was computed via singular value decomposition (as is standard in this case), [U,S,V]=svd(A), is performed on A that in turn finds a matrix of right singular vectors (U), a matrix of left singular vectors (V), and the singular value matrix (S).
3. Two different dimension reductions approaches are used: 1) Only include the largest eigenvalue (i.e. keep $\lambda_1$ and the remaining singular values are set to zero) and 2) the relative variance of each eigenvalue is computed and only eigenvalues greater than 1% of the total variation are kept, and all other eigenvalues are set to zero. For option (2), the largest 101-109 eigenvalues were selected in the 10-fold analysis.

Lastly, the PCA loads for the reduced set of eigenmodes are computed, and used along with the binary training labels $\{y_i, i=1, \ldots, n\}$ to train a two-class linear kernel SVM classifier. For all the reported results, a linear kernel SVM classifier was trained, and default parameters were used.

Comparison Results

FIG. 16 shows the results of the 10-fold cross-validation of HR-ASD vs HR-neg using the different methods discussed above on a reduced dataset (N=133). Referring to table 1600 in FIG. 16, DL+SVM is the proposed prediction pipeline; SL+SVM uses sparse learning (SL) for dimensionality reduction (i.e. feature selection) instead of DL; a deep classification network (DCN) that does not include a separate classification stage (see FIG. 13), and the two proposed PCA+SVM classifications.

The total number of subjects in the data set is 133 (27 HR-ASD subjects and 106 HR-neg subjects). The data set was partitioned into 10-folds where each fold has 12, 13, or 14 randomly selected subjects. Furthermore, the ratio of HR-ASD to HR-neg subjects in each fold is kept constant, or as similar as possible, to control the base rate and maintain the consistency of the learned decision boundary/space. Lastly, the binary diagnostic training labels used to train the prediction pipeline (i.e. deep network and SVM classifier) are 0=HR-ASD and 1=HR-neg.

The proposed prediction pipeline outperforms the other classification approaches as can be seen in Table 3.

2.5 HR-ASD/HR-Neg Pipeline Prediction Analysis Using Random Diagnosis Labels

Furthermore, we performed permutation based random diagnosis evaluation to check whether our prediction pipeline results are optimistically biased. We applied the above described 10-fold cross validation to randomly scrambled diagnosis labels via standard permutation analysis (both the deep network and the SVM classifier were retrained at every permutation). The random label scrambling was achieved using the Matlab random permutation (randperm) function.

Figure 14:
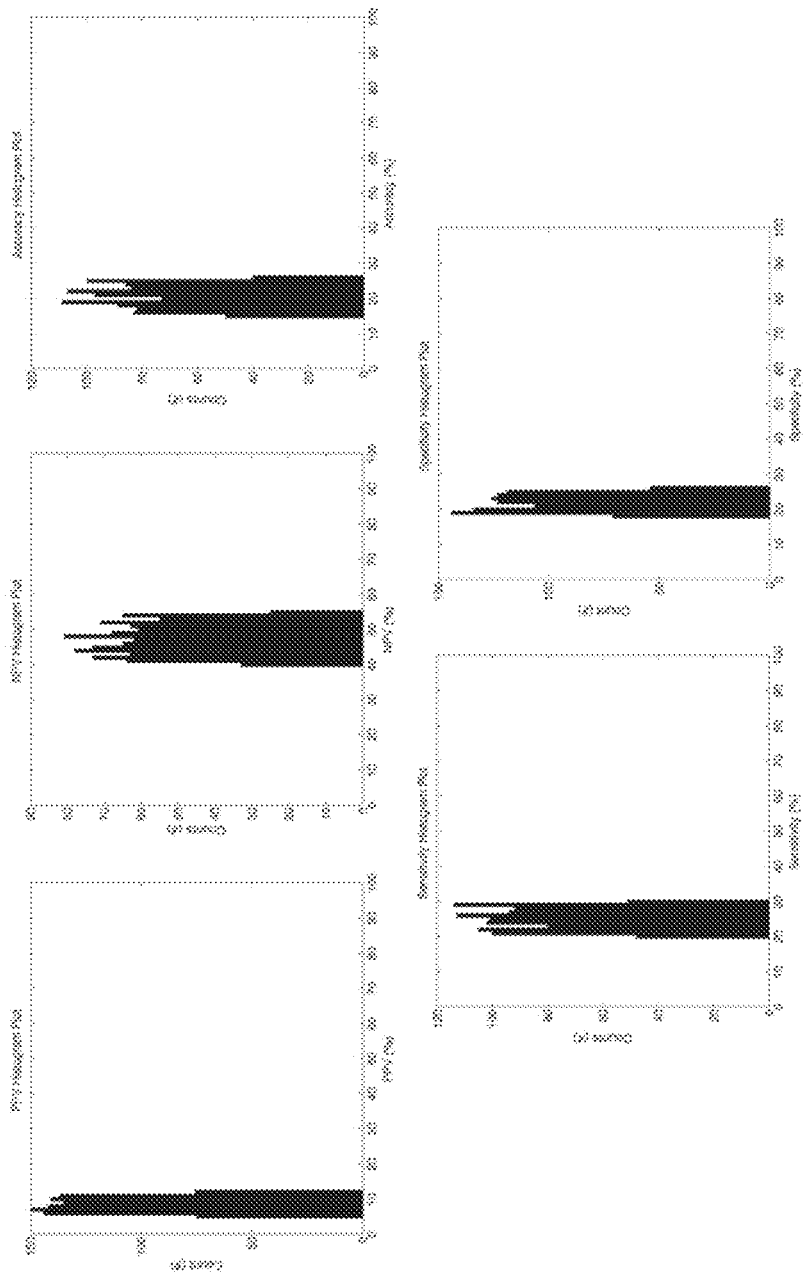
FIG. 14 depicts histogram plots of permutation analysis.

We employed 1,000 permutations, and the results for each measure (PPV, NPV, Accuracy, Sensitivity, and Specificity, average values of the 10-fold analysis) is visualized in the histogram plots shown in FIG. 14. In FIG. 14, histogram plots show the PPV, NPV, Accuracy (ACC), Sensitivity (SENS), and Specificity (SPEC) performance measures when the diagnosis labels are randomly scrambled in order to test whether the prediction results are optimistically biased. The random scrambling was repeated 1000 times and the corresponding statistics are shown in the histogram plots. No optimistic bias is detectable in this analysis as not a single random permutation reached comparable classification performance.

As seen in FIG. 14, the range of values over the 1,000 runs for the: 1) PPV measure was between 5 and 12 percent, 2) the NPV measure was between 40 and 55 percent, 3) the Accuracy measure was between 15 and 26 percent, 4) the Sensitivity measure was between 20 and 30 percent, and 5) the Specificity measure was between 18 and 26 percent. These results suggest the reported performance of our HR-ASD/HR-neg pipeline is identifying a pattern of longitudinal surface area, cortical thickness, ICV, and gender features that are expressed in HR-ASD subjects and that cannot be re-created using random labels, as not a single random permutation reached comparable classification performance.

Figure 15:
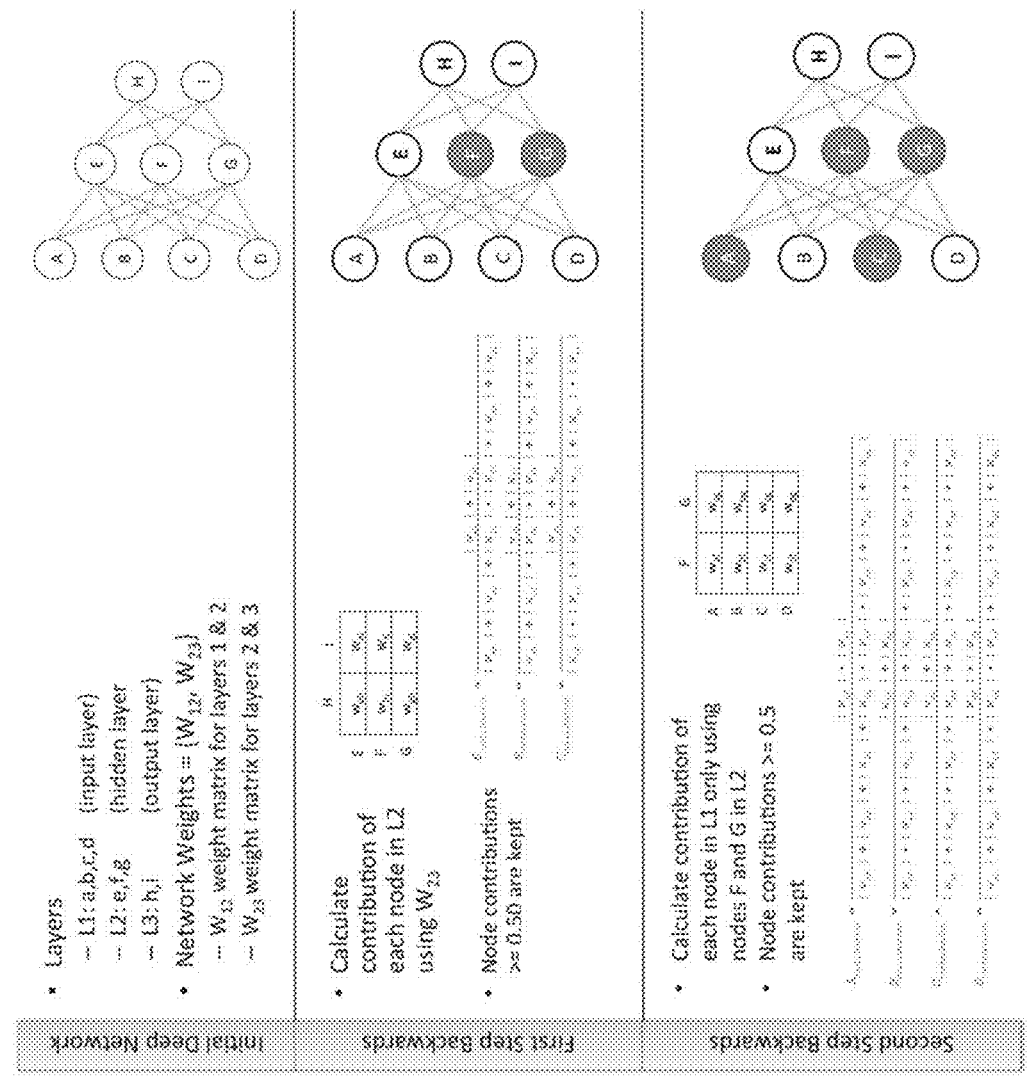
FIG. 15 depicts a procedure for estimating the nodes (or features) that contribute most to prediction accuracy.

2.6 Identifying High Dimension Features that Contribute to Prediction Performance Identifying which longitudinal CSA, CTH, ICV, and gender features defined in the high dimension feature vector have the greatest contribution (and the least contribution) to the LDC output by the fine-tuned DL network is a very challenging problem for deep non-linear dimensionality reduction approaches. To better understand how the input features are related to those defined in the LDC the following two approaches are used:

Approach 1 for our DL dimensionality reduction: Using the weight matrices in the fully trained DL network $\overline{N}=\{\overline{W}_1, \overline{W}_2, \ldots, \overline{W}_k\}$ we work backwards through the median DL network identifying only those nodes in the previous layer (e.g., l–1) that represent greater than 50% of the weight contribution layer l. FIG. 15 illustrates this process, using a simple example 3-layer network. FIG. 15 depicts a procedure for estimating the nodes (or features) in the input layer that contribute most to prediction accuracy. Using the weight matrices in the fully trained DL network we work backwards through the network identifying only those nodes in the previous layer that represent greater than 50% of the weight contribution to selected nodes in the current layer.

Approach 2 for the linear sparse learning approach: The sparse learning approach outperformed the PCA approach, we investigated also the features that were selected in that sparse learning. For this purpose we used an elastic net regularization, i.e.

$$\min_x \frac{1}{2}\|Ax-y\| + \frac{\rho}{2}\|x\|_2^2 + \lambda\|x\|_1,$$

the diagnosis labels y, and the trained two-stage sparse learning pipeline as follows:

Sequentially adjust the λ parameter defined in the $l_1$ regularization (sparsity) term between the values of 0.1 and 1.0 at increments of 0.1. For each increment, the learned sparse representation was applied to each high dimension feature vector in the test data set, and then the diagnosis labels for each sparse high dimension feature vector is predicted using trained two-stage pipeline and the PPV, NPV, and accuracy scores were stored.

The λ parameter that produced the highest PPV, NPV, and accuracy scores was then retrieved along with the learned sparse representation. In general, the selected features in the retrieved sparse representation provide insight about which high dimension longitudinal features contribute most to prediction performance.

The results in table 1700 in FIG. 17 show the top 40 features found by Approach 1 (non-linear deep learning), and the results in table 1800 in FIG. 18 show the top 40 features found by Approach 2 (linear sparse learning).

Comparing the two results, we can see agreement in several features, which likely/possibly drive the classification pipeline. Here we list the 7 features where both approaches agree and that are in the top 10 DL features: surface area at 6 months in the right and left superior frontal gyrus, post-central gyrus, and inferior parietal gyri, and ICV at 6 month.

Figure 19:
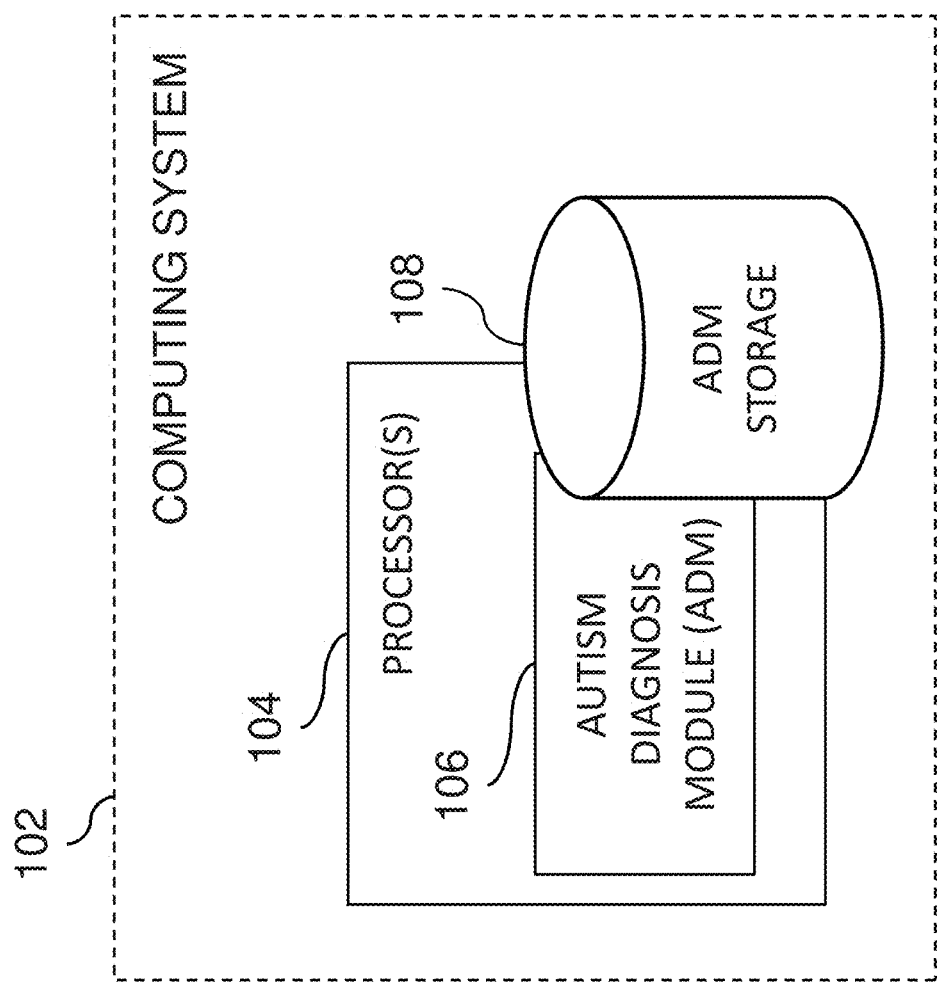
FIG. 19 is a diagram illustrating an example system for utilizing brain structural characteristics for predicting a diagnosis of a neurobehavioral disorder according to an embodiment of the subject matter described herein.

FIG. 19 is a diagram illustrating an example system 102 (e.g., a single or multiple processing core computing device) for utilizing brain structural characteristics for predicting a diagnosis of a neurobehavioral disorder according to an embodiment of the subject matter described herein. System 102 may be any suitable entity, such as a medical device or one or more computing devices or platforms, for performing one or more aspects of the present subject matter described herein or described in the attached manuscripts entitled "Brain Characteristics in the First Year Predict Early Neurobehavioral disorder diagnosis" and "Supplementary Information;" the disclosures of the attached manuscripts are incorporated herein by reference in their entireties.

In some embodiments, components, modules, and/or portions of system 102 may be implemented or distributed across multiple devices or computing platforms. For example, system 102 may involve multiple computers configured to perform various functions, such as obtaining magnetic resonance imaging (MRI) data, analyzing brain characteristics using the MRI data, generating brain related measurements, and/or predicting a neurobehavioral disorder diagnosis or an autism spectrum disorder (ASD) diagnosis using deep learning or neural network techniques.

In some embodiments, system 102 may include one or more processor(s) 104, a neurobehavioral disorder diagnosis module (ADM) 106, and an ADM storage 108. Processor(s) 104 may represent or include a physical processor, a general purpose microprocessor, a single-core processor, a multi-core processor, a field-programmable gate array (FPGA), and/or an application-specific integrated circuit (ASIC). In some embodiments, processor(s) 104 may be configured to execute software stored in one or more non-transitory computer readable media, such as ADM storage 108 in system 102. For example, software may be loaded into a memory structure for execution by processor(s) 104. In some embodiments, e.g., where system 102 includes multiple processors, some processor(s) 104 may be configured to operate independently of other processor(s) 104.

ADM 106 may be any suitable entity or entities (e.g., software executing on processor(s) 104, an ASIC, an FPGA, or a combination of software, an ASIC, or an FPGA) for performing one or more aspects associated with diagnosing autism using brain characteristics. In some embodiments, ADM 106 may be implemented using processor(s) 104 and/or one or more memories, such as ADM storage 108.

For example, ADM 106 may utilize processor(s) 104 (e.g., using software stored in local memory) and random access memory (RAM).

ADM 106 may include functionality for receiving brain imaging data for a human subject. For example, ADM 106 may receive brain imaging data from ADM storage 108 or an imaging data storage system. In another example, ADM 106 may include or communicate with an imaging system, such as an MRI scanner, to receive brain imaging data.

In some embodiments, ADM 106 may include or utilize one or more communications interfaces, e.g., one or more network interface cards (NICs), for interacting with various computers and/or other devices. For example, ADM 106 may use one or more communications interfaces for receiving and sending various types of data units; such as Internet protocol (IP) messages, Ethernet frames, Ethernet messages, or packet data units (PDUs). In another example, ADM 106 may utilize application programming interfaces (APIs) and/or graphical user interfaces (GUIs) to receive or obtain imaging data, such as MRI scans, and may use such interfaces to obtain information about a subject and/or to notify an entity (e.g., a medical worker and/or a subject's guardian) about a prediction regarding a neurobehavioral disorder diagnosis.

In some embodiments, ADM 106 may pre-process brain imaging data. For example, ADM 106 may trigger or perform rigid body co-registration of two MRIs of a subject's brain taken at around 6 months of age and at around 12 months of age to an atlas template. In this example, ADM 106 may trigger or perform correction of intensity inhomogeneity, and/or correction of geometric distortions for optimal processing of multi-site longitudinal data.

In some embodiments, ADM 106 may obtain and/or generate brain volumes and/or other measurements using brain imaging data and a framework of atlas-moderated expectation-maximization. For example, ADM 106 may utilize a framework of atlas-moderated expectation-maximization that includes, among other steps, co-registration of a first set of imaging data (e.g., an MRI scan of a subject's brain at 12 months old) to a second set of imaging data (e.g., an MRI scan of the subject's brain at 6 months old).

In some embodiments, ADM 106 may include functionality for determining, from brain imaging data, measurements of brain structural characteristics of the subject. In some embodiments, ADM 106 may obtain and/or generate brain related measurements associated with surface area and cortical thickness. For example, ADM 106 may utilize a CIVET workflow to generate cortical thickness and surface area measurements for different imaging data (e.g., MRI scans at 6 months of age and at 12 months of age). In this example, ADM 106 may adapt measurements using an age-corrected, automated, anatomical labeling (AAL) atlas.

In some embodiments, ADM 106 may utilize a CIVET workflow that includes shrink-wrap deformable surface evolution of white (brain) matter, local Laplacian distance and local surface area, mapping to a spherical domain, co-registration using cortical sulcal features and extraction of regional measurements via a deformably co-registered fine-scale lobar parcellation. In some embodiments, surface area may be measured at the mid-cortical surface averaged from the computed white and pial surfaces.

In some embodiments, ADM 106 may input brain structural characteristics into a model that predicts, using the measurements of the brain structural characteristics, a diagnosis of a neurobehavioral disorder at a second age greater than the at least one first age.

In some embodiments, ADM 106 may utilize a machine learning algorithm and/or a non-linear prediction model for predicting a diagnosis of a neurobehavioral disorder. For example, a non-linear projection model may use various unbiased/unweighted information, e.g., the sex of a subject, age-corrected intracranial volume (ICV), and age-corrected surface area and cortical thickness measurements from 39 left and 39 right cortical hemisphere regions at 6 months of age and 12 months of age, e.g., which may total approximately 315 measurements for any given subject. In this example, the non-linear projection model may be evaluated via a standard ten-fold cross-validation.

In some embodiments, ADM 106 may utilize a non-linear projection model that uses a weighted three-stage deep learning network. For example, in a three-stage deep learning network may include a first stage that reduces 315 measurements to 100 measurements, a second stage that reduces 100 measurements to 10 measurements, and a third stage that reduces 10 measurements to 2 measurements. In this example, at each stage, the measurements (in the progressively smaller sets) may be the weighted combination of input measurements from a previous stage.

In some embodiments, ADM 106 or a related entity may train a deep learning network using various brain imaging data and/or brain measurements prior to using the network for predicting autism or an ASD. For example, training a deep learning network may involve determining network weights that retain information associated with an optimal reconstruction of data when inverting the network (e.g., auto-encoding) and may also involving determining a linear support vector machine based classification decision that separates group labels, e.g., "high risk and positive for ASD (HR-ASD)" and "high risk and negative for ASD (HR-NEG)", in a two dimensional network space.

In some embodiments, after training a deep learning network, ADM 106 may apply a non-linear projection model by inserting brain imaging data or related measurements into the two dimensional network space and then classifying measurements in the final network space using a trained support vector machine.

ADM storage 108 may be any suitable entity or entities (e.g., one or more memory devices) for storing information associated with diagnosing autism or an ASD using brain characteristics. For example, ADM storage 108 may store one or more machine learning algorithms, MRI data or other medical imaging data, various subject (e.g., patient) information, and/or diagnosis related information. In another example, ADM storage 108 may store information about testing, treatments, or interventions.

It will be appreciated that FIG. 19 is for illustrative purposes and that various nodes, their locations, and/or their functions may be changed, altered, added, or removed. For example, some nodes and/or functions may be combined into a single entity. In a second example, a node and/or function may be located at or implemented by two or more nodes.

Figure 20:
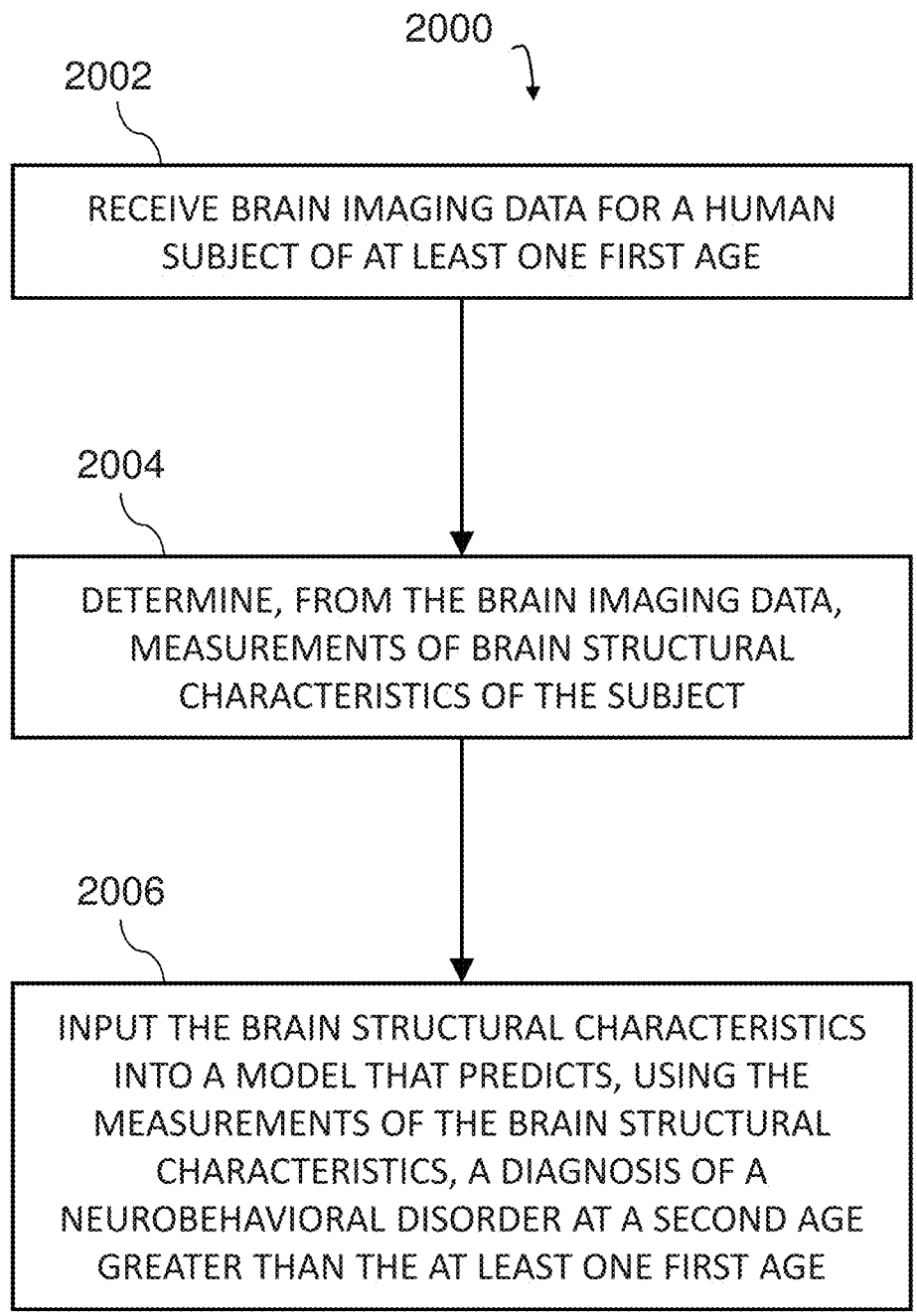
FIG. 20 is a diagram illustrating an example process for utilizing brain structural characteristics for predicting a diagnosis of a neurobehavioral disorder according to an embodiment of the subject matter described herein.

FIG. 20 is a diagram illustrating an example process 2000 for utilizing brain structural characteristics for predicting a diagnosis of a neurobehavioral disorder according to an embodiment of the subject matter described herein. In some embodiments, process 2000, or portions thereof, may be performed by or at system 102, a computer communicatively connected to system 102, or another node.

Referring to FIG. 20, in step 2002, brain imaging data for a human subject of at least one first age may be received. For example, brain imaging data may include information indicating changes (e.g., brain volume growth) over a period of time. For example, brain imaging data may include imaging data (e.g., a first MRI scan) associated with a subject's brain at around six months of age and imaging data (e.g., a second MRI scan) associated with the subject's brain at around twelve months of age.

In some embodiments, at least one first age may comprise ages at which a subject does not exhibit classical behavioral symptoms of a neurobehavioral disorder. For example, at the time when brain imaging data is obtained, a human subject may be presymptomatic and/or may be under two years old.

In step 2004, determining, from the brain imaging data, measurements of brain structural characteristics of the subject. In some embodiments, determining measurements of brain structural characteristics of a human subject may include generating measurements associated with surface area and cortical thickness. For example, such measurements may be generated using a CIVET workflow and/or using an age corrected anatomical labeling (AAL) atlas.

In step 2006, the brain structural characteristics may be inputted into a model that predicts, using the measurements of the brain structural characteristics, a diagnosis of a neurobehavioral disorder at a second age greater than the at least one first age. For example, at least one first age may comprise six months and twelve months and a second age may comprise an age of two years or more.

In some embodiments, a model used for predicting diagnosis of a neurobehavioral disorder may use a machine learning algorithm.

In some embodiments, a machine learning algorithm may use a non-linear prediction model.

In some embodiments, a machine learning algorithm may utilize a weighted three-stage deep learning network, wherein a subsequent stage uses a progressively smaller number of measurements than a previous stage.

In some embodiments, a neurobehavioral disorder may include an autism spectrum disorder, a neurological developmental disorder, or a behavioral disorder.

In some embodiments, after predicting a neurobehavioral disorder diagnosis associated with a subject, an intervention action may be performed based on the predicted neurobehavioral disorder diagnosis. For example, an intervention action may include scheduling a subject for further testing, initiating an intervention or treatment, or notifying a medical worker about the diagnosis.

It should be noted that system 102, ADM 106, and/or functionality described herein may constitute a special purpose computing device.

Further, system 102, ADM 106, and/or functionality described herein can improve the technological field of early autism detection.

Each of the following references is incorporated herein by reference in its entirety:

REFERENCES

1. Developmental Disabilities Monitoring Network Surveillance Year 2010 Principal Investigators; Centers for Disease Control and Prevention (CDC). Prevalence of autism spectrum disorder among children aged 8 years—Autism and Developmental Disabilities Monitoring Network, 11 sites, US (2010).
2. Piven, J. et al. Magnetic resonance imaging in autism: Measurement of the cerebellum, pons, and fourth ventricle. *Biol Psychiatry.* 31, 491-504 (1992).
3. Piven, J. et al. An MRI study of brain size in autism. *Am J Pyschiatry.* 152(8), 1145-1149 (1995).
4. Courchesne, E. et al. Unusual brain growth patterns in early life in patients with autistic disorder: An MRI study. *Neurology.* 57, 245-254 (2001).
5. Hazlett, H. C. et al. Magnetic resonance imaging and head circumference study of brain size in autism: birth through age 2 years. *Arch Gen Psychiatry.* 62 (12), 1366-1376 (2005).
6. Hazlett, H. C. et al. Early brain overgrowth in autism associated with an increase in cortical surface area before age 2 years. *Arch Gen Psychiatry.* 68 (5), 467-476 (2011).
7. Schumann, C. M. et al. Longitudinal magnetic resonance imaging study of cortical development throuhg early childhood in autism. *J Neurosci.* 30 (12), 4419-4427 (2010).
8. Sparks, B. et al. Brain structural abnormalities in young children with autism spectrum disorder. *Neurology.* 59 (2), 184-192 (2002).
9. Shen, M. D. et al. Early brain enlargement and elevated extra-axial fluid in infants who develop autism spectrum disorder. *Brain.* 136(9), 2825-2835 (2013).
10. Ozonoff, S. et al. A prospective study of the emergence of early behavioral signs of autism. *J Am Acad Child Adolesc Psychiatry.* 49 (3), 256-266 (2010).
11. Zwaigenbaum, L. et al. Behavioral manifestations of autism in the first year of life. *Int J Dev Neurosci.* 23(2-3): 143-152 (2005).
12. Constantino, J. N. et al. Infant head growth in male siblings of children with and without autism spectrum disorders. *J Neurodev Disord.* 2(1), 39-46 (2010).
13. Mullen, E M. Mullen Scales of Early Learning (AGS ed.). Circle Pines, Minn.: American Guidance Service, Inc. (1995).
14. Sparrow, S., Balla, D., & Cicchetti, D. Vineland scales of adaptive behavior: A survey form manual. Circle Pines, Minn.: American Guidance Service, Inc. (1984).
15. Messinger, D. et al. Beyond autism: a baby siblings research consortium study of high-risk children at three years of age. *J Am Acad Child Adolesc Psychiatry.* 52(3), 300-308 (2013).
16. Georgiades, S. et al. A prospective study of autistic-like traits in unaffected siblings of probands with autism spectrum disorder. *JAMA Psychiatry.* 70(1), 42-48 (2013).
17. Lord, C., Rutter M., DiLavore, P.C., Risi, S. The Autism Diagnostic Observation Schedule. Los Angeles, Calif., Western Psychological Services. (2000).
18. Constantino, J.N. The quantitative nature of autistic social impairment. *Pediatric research.* 69 (5 Pt2), 55R-62R (2011).
19. Tzourio-Mazoyer, N. et al. Automated anatomical labeling of activations in SPM using a macroscopic anatomical parcellation of the MNI MRI single-subject brain. *NeuroImage.* 15(1), 273-289 (2002).
20. Benjamini, Y., Krieger, A.M., & Yekutieli, D. Adaptive linear step-up procedures that control the false discovery rate. *Biometricka.* 93(3), 491-507 (2006).
21. Wetherby, A., & Prizant, B. Communication and symbolic behavior scales developmental profile—First normed edition. Baltimore, Md.: Paul H. Brookes. (2002).
22. Hinton, G.E., & Salakhutkinov, R.R. Reducing the dimensionality of data with neural networks. *Science.* 313(5786), 504-507 (2006).
23. Cortes, C., & Vapnik, V. Support-vector networks. *Machine Learning.* 20(3), 273-297 (1995).
24. Li, G. et al. Mapping longitudinal hemispheric structural asymmetries of the human cerebral cortex from birth to 2 years of age. *Cereb Cortex.* 24(5), 1289-1300 (2014).

25. Elison, J. T. et al. White matter microstructure and atypical visual orienting in 7-month-olds at risk for autism. *Am J Psychiatry.* 170(8), 899-908 (2013).
26. Wolff, J. J. et al. Longitudinal patterns of repetitive behavior in toddlers with autism. *J Child Psychol Psychiatry.* 55(8), 945-953 (2014).
27. Estes, A. et al. Behavioral, cognitive, and adaptive development in infants with autism spectrum disorder in the first two years of life. *J Neurodev Disorders.* 7(1), 24 (2015).
28. Karmel, B. Z. et al. Early medical and behavioral characteristics of NICU infants later classified with ASD. *Pediatrics.* 126(3), 457-467 (2010).
29. Qureshi, A. Y. et al. Opposing brain differences in 16p11.2 deletion and duplication carriers. *J Neurosci.* 34(34), 11199-11211 (2014).
30. Mirzaa, G.M., & Poduri, A. Megalencephaly and hemimegalencephaly: breakthroughs in molecular etiology. *Am J Med Genet C Semin Med Genet.* 166C(2), 156-172 (2014).
31. Bernier, R. et al. Disruptive CHD8 mutations define a subtype of autism early in development. *Cell.* 158(2), 263-276 (2014).
32. Panizzon, M. S. et al. Distinct genetic influences on cortical surface area and cortical thickness. *Cereb Cortex.* 11, 2728-2735 (2009).
33. Winkler, A. M. et al. Cortical thickness or grey matter volume? The importance of selecting the phenotype for imaging genetics studies. *Neuroimage.* 53, 1135-1146 (2010).
34. Rakic, P. A small step for the cell, a giant leap for mankind: a hypothesis of neocortical expansion during evolution. *Trends Neurosci.* 18, 383-388 (1995).
35. Chenn, A., Walsh, C.A. Regulation of cerebral cortical size by control of cell cycle exit in neural precursors. *Science.* 297: 365-369 (2002).
36. Kim, W.Y., Snider, W.D. Functions of GSK-3 signaling in development of the nervous system. *Front Mol Neurosci.* 4: 44 (2011).
37. Casanova, M. F. et al. Minicolumnar abnormalities in autism. *Acta Neuropathol.* 112(3): 287-303 (2006).
38. Hill, J. et al. Similar patterns of cortical expansion during human development and evolution. *Proc Natl Acad Sci.* 107(29), 13135-13140 (2010).
39. Fan, W. Q. et al. Overproduction of upper-layer neurons in the neortex leads to autism-like features in mice. *Cell Rep.* 9(5): 1635-1643. (2014).
40. Pucilowska, J., Puzery, P.A., Karlo, J.C., Galan, R.F., Landreth, G.E. The 16p11.2 deletion mouse model of autism exhibits altered cortical progenitor proliferation and brain cytoarchitecture linked to the ERK MAPK patheway. *J Neurosci.* 35(7): 3190-2100. (2015).
41. Nonaka-Kinoshita, M. et al. Regulation of cerebral cortex size and folding by expansion of basal progenitors. *EMBO J.* 32 (13), 1817-1828 (2013).
42. Sugathan, A. et al. CHD8 regulates neurodevelopmental pathways associated with autism spectrum disorder in neural progenitors. *Proc Natl Acad Sci.* 111(42), E4468-E4477 (2014).
43. Cotney, J. et al. The autism-associated chromatin modifier CHD8 regulates other autism risk genes during human neurodevelopment. *Nature Commun.* 6, 6406 (2015).
44. Charman, T. Early identification and intervention in autism spectrum disorders: Some progress but not as much as we hoped. *Int J Speech Lang Pathol.* 16 (1), 15-18 (2014).
45. Turner-Brown, L.M., Baranek, G.T., Reznick, J.S., Watson, L.R., & Crais, E.R. The First Year Inventory: a longitudinal follow-up of 12-month-old to 3-year-old children. *Autism.* 17(5), 527-540 (2013).
46. Charwarska, K. et al. 18-month predictors of later outcomes in younger siblings of children with autism spectrum disorder: A baby siblings research consortium study. *J Am Acad Child Adolesc Psychiatry.* 53(12), 1317-1327 (2014).
47. Yirmiya, N., & Charman, T. The prodrome of autism: early behavioral and biological signs, regression, peri- and post-natal development and genetics. *J Child Psychol Psychiatry.* 51(4), 432-458 (2010).
48. Landa, R.J., Gross, A.L., Stuart, E.A., & Faherty, A. Developmental trajectories in children with and without autism spectrum disorders: the first 3 years. *Child Dev.* 84(2), 429-442 (2013).
49. Ozonoff, S., et al. The broader autism phenotype in infancy: When does it emerge? *J Am Acad Child Adolesc Psychiatry.* 53(4), 398-407 (2014).
50. Hazlett, H. C. et al. Brain volume findings in 6-month-old infants at high familial risk for autism. *Am J Psychiatry.* 169, 601-608 (2012).
51. Lord, C., Rutter, M., & LeCouteur, A. Autism Diagnostic Interview-Revised: a revised version of a diagnostic interview for caregivers of individuals with possible pervasive developmental disorders. *J Autism Dev Disord.* 24, 659-685 (1994).
52. Guthri, W., Swineford, L.B., Nottke, C., & Wetherby, A. Early diagnosis of autism spectrum disorder: stability and change in clinical diagnosis and symptom presentation. *J Child Psychol Psychiatry.* 54(5), 582-590 (2013).
53. Wang, J. et al. Multi-atlas segmentation of subcortical brain structures via the AutoSeg software pipeline. *Front Neuroinform.* 8, 7 (2014).
54. Shaw, P. et al. Development of cortical surface area and gyrification in attention-deficit/hyperactivity disorder. *Biol Psychiatry.* 72(3), 191-197 (2012).
55. Shaw, P. et al. Neurodevelopmental trajectories of the human cerebral cortex. *J Neurosci.* 28(14), 3586-94 (2008).
56. Kim, S. H. et al. Adaptive prior probability and spatial temporal intensity change estimation for segmentation of the one-year-old human brain. *J Neurosci Methods.* 212 (1): 43-455 (2013).
57. Avants, B.B., Epstein, C.L., Grossman, M., & Gee, J.C. Symmetric diffeomorphic image registration with cross-correlation: evaluating automated labeling of elderly and neurodegenerative brain. *Med Image Anal.* 12(1), 26-41 (2008).
58. Im, K., et al. Brain size and cortical structure in the adult human brain. *Cerebral Cortex.* 18: 2181-2191 (2008).
59. Chawarska, K., et al. Early generalized overgrowth in boys with autism. *Arch of Gen Psych,* 68(10), 1021-31. (2011).
60. Raznahan, A., et al. Compared to what? Early brain overgrowth in autism and the perils of population norms. *Biological Psychiatry.* 74(8), 563-75. (2013).
61. R. C. Knickmeyer, S. Gouttard, C. Kang, D. Evans, K. Wilber, J. K. Smith, R. M. Hamer, W. Lin, G. Gerig, and J. H. Gilmore, "A structural MRI study of human brain development from birth to 2 years.," J Neurosci, vol. 28, no. 47, pp. 12176-12182, November 2008.
62. American Psychiatric Association (2000). Diagnostic and statistical manual of mental disorders ($4^{th}$ ed., text rev.). Washington, D.C.

63. Im K., et al. Brain size and cortical structure in the adult human brain. *Cerebral Cortex.* 18: 2181-2191 (2008).
64. Gilmore, J. H., et al. Regional gray matter growth, sexual dimorphism, and cerebral asymmetry in the neonatal brain. *J Neurosci.* 27(6), 1255-1260 (2007).
65. Kim, S. H., et al. Adaptive prior probability and spatial temporal intensity change estimation for segmentation of the one-year-old human brain. *J Neurosci Methods.* 212 (1), 43-55 (2013).
66. Tustison, N. J., et al. N41TK: improved N3 bias correction. *IEEE Transactions on Medical Imaging.* 29(6), 1310-1320 (2010).
67. Fonov, V., et al. Improved precision in the measurement of longitudinal global and regional volumetric changes via a novel MRI gradient distortion characterization and correction technique. *Computer Vision—Accv 2006, Pt I,* 6326, 324-333. (2010).
68. Fonov, V., et al. Unbiased average age-appropriate atlases for pediatric studies. *NeuroImage.* 54(1), 313-327 (2011).
69. Shaw, P. et al. Development of cortical surface area and gyrification in attention-deficit/hyperactivity disorder. *Biol Psychiatry.* 72(3), 191-197 (2012).
70. Shaw, P. et al. Neurodevelopmental trajectories of the human cerebral cortex. *J Neurosci.* 28(14), 3586-94 (2008).
71. Tzourio-Mazoyer, N. et al. Automated anatomical labeling of activations in SPM using a macroscopic anatomical parcellation of the MNI MRI single-subject brain. *NeuroImage.* 15(1), 273-289 (2002).
72. Avants, B. B., et al. A reproducible evaluation of ANTs similarity metric performance in brain image registration. *NeuroImage.* 54(3), 2033-2044. (2011).
73. Hazlett, H. C, et al. Early brain overgrowth in autism associated with an increase in cortical surface area before age 2 years. *Arch Gen Psychiatry.* 68(5): 467-76 (2011).
74. Fishbaugh, J., Durrleman, S., Piven, J., Gerig, G. A framework for longitudinal data analysis via shape regression. Proc. SPIE 8314, Medical Imaging 2012: Image Processing.
75. Giedd, J. N., et al. Brain development during childhood and adolescence: a longitudinal MRI study. *Nature Neuroscience.* 2: 861-863 (1999).
76. Hinton, G.E., Salakhutdinov, R.R. Reducing the Dimensionality of Data with Neural Networks. *Science.* 313 (5786): 504-507 (2006).
77. Hoo-Chang Shin, M. R. Orton, D. J. Collins, S. J. Doran, M. O. Leach, "Stacked Autoencoders for Unsupervised Feature Learning and Multiple Organ Detection in a Pilot Study Using 4D Patient Data," *IEEE Transactions on Pattern Analysis and Machine Intelligence,* 35(8):1930-1943 (2013).
78. Dan C. Ciresan, Alessandro Giusti, Luca M. Gambardella, Jurgen Schmidhuber, "Mitosis Detection in Breast Cancer Histology Images with Deep Neural Networks", MICCAI 2013, Nagoya, Japan
79. Zou, H., & Hastie, T. Regularization and variable selection via the elastic net. *J of the Royal Statistical Society. Series B, Statistical Methodology.* 67(2), 301-320. (2005).
80. Li, Train, Thung, Ji, Shen, Li, "Robust deep learning for improved classification of AD/MCI patients", Machine Learning in Medical Imaging (MLMI) Workshop, Lecture Notes in Computer Science, Vol 8679, pp 240-247, 2014
81. Suk, Shen, "Deep learning-based feature representation for AD/MCI classification", Medical Image Computing and Computer Assisted Intervention (MICCAI), Lecture Notes in Computer Science, Vol 8150, pp 583-590, 2013
82. Lee, Lagman, Pham, Ng, "Supervised feature learning for audio classification using convolutional deep belief networks", Advances in neural information processing systems (NIPS), 2009.
83. Lee, Gross, Ranganath, Ng, "Convolutional deep belief networks for scalable unsupervised learning of hierarchical representations", 26th Annual International conference on Machine Learning (ICML), pp 609-616, 2009
84. Hao, Raiko, Ilin, Karhunen, "Gated Boltzmann Machine in Texture Modeling", International Conference on Artificial Neural Networks and Machine Learning, (ICANN), Lecture Notes in Computer Science, Vol 7553, pp 124-131, 2012
85. Huang, Lee, Learned-Miller, "Learning hierarchical representations for face verification with convolutional deep belief networks", IEEE Conference on Computer Vision and Pattern Recognition (CVPR), pp. 2518-2525, 2012
86. Gan, Li, Zhai, Liu, "Deep self-taught learning for facial beauty prediction", Neurocomputing, Vol. 144, pp. 295-303, 2014.
87. Hinton, "*A Practical Guide to Training Restricted Boltzmann Machines*", UTML TR 2010-003, Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for utilizing brain structural characteristics for predicting a diagnosis of a neurobehavioral disorder, the system comprising:
   at least one processor; and
   a neurobehavioral disorder diagnosis module (NDDM) implemented using the at least one processor, wherein the NDDM is configured for receiving brain imaging data for a human subject when the human subject is about 6 months of age and when the human subject is about 12 months of age, for determining, from the brain imaging data, measurements of brain structural characteristics of the human subject, and for inputting the brain structural characteristics into a model that predicts, using the measurements of the brain structural characteristics, a diagnosis of a neurobehavioral disorder at a third age greater than the about 12 months of age, wherein the model takes as input a first feature vector containing cortical thickness and surface area measurements from multiple brain regions based on the brain imaging data, wherein the model generates, using the first feature vector, a second feature vector indicating a cortical thickness growth pattern and a surface area thickness growth pattern and wherein the model uses the second feature vector to predict the diagnosis, wherein the model is generated using a machine learning algorithm, wherein the machine learning algorithm utilizes a weighted three-stage deep learning network, wherein a subsequent stage uses a progressively smaller number of measurements than a previous stage and wherein the neurobehavioral disorder comprises an autism spectrum disorder.

2. The system of claim 1 wherein the NDDM is configured for performing an intervention action based on the predicted neurobehavioral disorder diagnosis.

3. The system of claim 1 wherein the third age comprises an age of two years or more.

4. The system of claim 1 wherein the measurements are generated using an age corrected anatomical labeling (AAL) atlas.

5. The system of claim 1 wherein the machine learning algorithm utilizes a weighted three-stage deep learning network, wherein a subsequent stage uses a progressively smaller number of measurements than a previous stage.

6. The system of claim 1 wherein the model includes a non-linear prediction model.

7. The system of claim 1 wherein the about 6 months of age and the about 12 months of age comprise ages at which the human subject does not exhibit classical behavioral symptoms of the neurobehavioral disorder.

8. The system of claim 1 wherein the neurobehavioral disorder comprises a neurological developmental disorder, or a behavioral disorder.

* * * * *